United States Patent
Larsen et al.

(10) Patent No.: US 10,941,137 B2
(45) Date of Patent: Mar. 9, 2021

(54) DIFLUOROMETHYL-PHENYL TRIAZOLES

(71) Applicant: Boehringer Ingelheim International GmbH, Ingelheim am Rhein (DE)

(72) Inventors: Janus Schreiber Larsen, Holbæk (DK); Florian Binder, Ingelheim am Rhein (DE); Yunhai Cui, Ingelheim am Rhein (DE); Oliver Hucke, Ingelheim am Rhein (DE); Radoslaw Lipinski, Ingelheim am Rhein (DE); Florian Montel, Ingelheim am Rhein (DE); Markus Ostermeier, Ingelheim am Rhein (DE); Alexandre Perera, Ingelheim am Rhein (DE); Stefan Peters, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/516,398

(22) Filed: Jul. 19, 2019

(65) Prior Publication Data
US 2020/0024261 A1 Jan. 23, 2020

(30) Foreign Application Priority Data

Jul. 20, 2018 (EP) .................................. 18184716

(51) Int. Cl.
| | |
|---|---|
| *A61K 31/4192* | (2006.01) |
| *A61K 31/501* | (2006.01) |
| *A61K 31/4155* | (2006.01) |
| *A61K 31/4178* | (2006.01) |
| *A61K 31/4196* | (2006.01) |
| *A61K 31/421* | (2006.01) |
| *A61K 31/437* | (2006.01) |
| *A61K 31/497* | (2006.01) |
| *A61K 31/506* | (2006.01) |
| *A61K 31/4439* | (2006.01) |
| *A61K 31/444* | (2006.01) |
| *A61P 25/00* | (2006.01) |
| *C07D 403/14* | (2006.01) |
| *C07D 401/14* | (2006.01) |
| *C07D 471/04* | (2006.01) |

(52) U.S. Cl.
CPC ........ *C07D 403/14* (2013.01); *C07D 401/14* (2013.01); *C07D 471/04* (2013.01)

(58) Field of Classification Search
CPC .............. A61K 31/4192; A61K 31/501; A61K 31/4155; A61K 31/4178; A61K 31/4196; A61K 31/421; A61K 31/437; A61K 31/497; A61K 31/506; A61K 31/4439; A61K 31/444; A61P 25/00; C07D 403/14; C07D 401/14; C07D 471/04
See application file for complete search history.

(56) References Cited

U.S. PATENT DOCUMENTS

2009/0143385 A1 6/2009 Buettemann et al.

FOREIGN PATENT DOCUMENTS

WO WO 2012/062687 A1 5/2012

OTHER PUBLICATIONS

International Search Report and Written Opinion for Application No. PCT/EP2019/069593 dated Aug. 30, 2019.

*Primary Examiner* — Brenda L Coleman
(74) *Attorney, Agent, or Firm* — Wolf, Greenfield & Sacks, P.C.

(57) ABSTRACT

The present invention relates to difluoromethyl-phenyl triazoles of general formula (I) which are modulators of $GABA_A$ receptors containing the α5 subunit, useful in treating central nervous system diseases and other diseases. In addition, the invention relates to processes for preparing pharmaceutical compositions as well as processes for manufacture the compounds according to the invention.

3 Claims, No Drawings

DIFLUOROMETHYL-PHENYL TRIAZOLES

CROSS REFERENCE TO RELATED APPLICATION

The present application claims priority to European Application No. 18184716.1, filed Jul. 20, 2018. The entire contents of these applications are incorporated herein by reference in their entirety.

FIELD OF THE INVENTION

The present invention relates to difluoromethyl-phenyl triazoles of general formula (I) which are modulators of $GABA_A$ receptors containing the α5 subunit, useful in treating central nervous system diseases and other diseases. In addition, the invention relates to processes for preparing pharmaceutical compositions as well as processes for manufacture the compounds according to the invention.

BACKGROUND OF THE INVENTION

In literature it has been suggested that the $GABA_A$ α5 subunit represents a therapeutic target for treatment of various diseases and disorders of the central nervous system, and a nexus has been established between the $GABA_A$ α5 subunit as therapeutic target, and various neurological disorders, disorders of circadian rhythms, pain conditions, and compounds capable of modulating $GABA_A$ receptors containing the α5 subunit are in particular expected to be useful candidates for the treatment of i.a. cognitive disorders, Alzheimer's disease, schizophrenia, positive, negative and/or cognitive symptoms associated with schizophrenia, cognitive impairment associated with schizophrenia and cognitive deficits associated with Down syndrome, with autism, with neurofibromatosis type I, or after stroke (see e.g. Neuroscience Letts. (2005) 81:108-13, Neuropsychobiology (2001) 43(3):141-44, Amer. J. Med. Genetics (2004) 131B: 51-9, Autism (2007) 11 (2): 135-47, Investigacion Clinica (2007) 48:529-41, Nature Neuroscience (2007) 10:411-13, Neuroscience Letts. (2008) 433: 22-7, Cell (2008) 135:549-60).

Isoxazole derivatives capable of modulating the $GABA_A$ receptor complex are known from e.g. WO 2007/039389, WO 2007/042420, WO 2007/054444, WO 2007/071598, WO 2007/074078, WO 2007/074089, WO 2007/137954, WO 2009/000662, WO 2009/071464, WO 2009/071476, WO 2009/071477, WO 2010/097368, WO 2010/112475, WO 2010/125042, WO 2010/127968, WO 2010/127974, WO 2010/127975, WO 2010/127976, WO 2010/127978, WO 2012/059482 and WO 2018/104419. Phenyl-triazole derivatives capable of modulating the $GABA_A$ receptor complex are known from e.g. WO 2012/062687, WO 2014/001281 and WO 2014/001282. Moreover, WO 2007/140174, WO 2008/025539, WO 2008/025540, WO 2009/149795 and WO 2011/020615 describe heterocyclic compounds, including certain phenyl triazole derivatives, useful as agonists of the NR1H4 (FXR) receptor. Further structurally related compounds are disclosed in WO2012/133607 as PDE10a inhibitors.

AIM OF THE INVENTION

Surprisingly it has been found that phenyl-triazoles of the general formula (I),

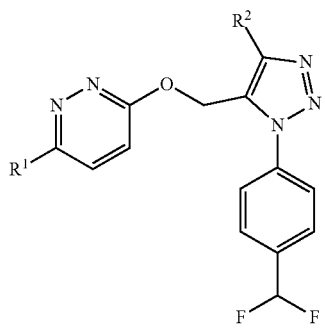

wherein $R^1$ is a heteroarylgroup and the phenylgroup bears a difluoromethylgroup are excellent negative modulators of the $GABA_A5R$ (i.e. negative modulator of the $GABA_A$ α5 subunit) having improved properties with respect to $GABA_A5R$ binding properties, which translates in lower efficacious doses of the compounds for disease treatment, and as a consequence in advantages such as minimization of side effects. Furthermore, the compounds of the present invention have excellent CNS penetration with low efflux ratio from the brain compartment which is necessary for drugs with an intended action in the CNS and a high metabolic stability. Furthermore the compounds have very high IC50 values for the Cytochrome P450 3A4, 2C8, 2C9, 2D6 and 2C19.

Accordingly, one aspect of the invention refers to compounds according to formula (I), or salts thereof as negative modulators of the $GABA_A5R$.

Another aspect of the invention refers to compounds according to formula (I), or pharmaceutically acceptable salts thereof as negative modulators of the $GABA_A5R$ with high $GABA_A5R$ binding properties Another aspect of the invention refers to compounds according to formula (I), or pharmaceutically acceptable salts thereof as negative modulators of the $GABA_A5R$ with high $GABA_A5R$ binding properties and excellent CNS penetration with low efflux ratio from the brain compartment and a high metabolic stability and/or very high IC50 values for the Cytochrome P450 3A4, 2C8, 2C9, 2D6 and 2C19.

In a further aspect this invention relates to pharmaceutical compositions, containing at least one compound according to formula (I), or pharmaceutically acceptable salts thereof, optionally together with one or more inert carriers and/or diluents.

Another aspect of the invention relates to processes of manufacture of the compounds of the present invention.

A further aspect of the present invention relates to compounds according to formula (I), or pharmaceutically acceptable salts thereof or pharmaceutical compositions comprising compounds according to formula (I), or pharmaceutically acceptable salts thereof for the use in the prevention and/or treatment of diseases or conditions which can be influenced by negative modulation of the $GABA_A5R$ such as acute neurological disorders, chronic neurological disorders, cognitive disorders, Alzheimer's disease, memory deficits, schizophrenia, positive, negative and/or cognitive symptoms associated with schizophrenia, cognitive impairment associated with schizophrenia, bipolar disorders, autism, Down syndrome, neurofibromatosis type I, post operative cognitive decline, sleep disorders, disorders of circadian rhythms, amyotrophic lateral sclerosis, dementia caused by AIDS, psychotic disorders, substance-induced psychotic disorder, anxiety disorders, generalized anxiety disorder, panic disorder, delusional disorder, obsessive compulsive disorders, acute stress disorder, drug addictions, movement disorders, Parkinson's disease, restless leg syndrome, cognition deficiency disorders, multi-infarct dementia, mood disorders, depression, major depressive disorder, neuropsychiatric conditions, psychosis, attention-deficit hyperactivity disorder, neuropathic pain, stroke, attentional disorders, eating disorders, anorexia, anorexia nervosa, cachexia, weight loss, muscle atrophy, pain conditions, chronic pain, nociceptive pain, post-operative pain, osteoarthritis pain, rheumatoid arthritis pain, musculoskeletal pain, burn pain, ocular pain, pain due to inflammation, pain due to bone fracture, hyperalgesia, neuropathic pain, herpes-related pain, HIV-related neuropathic pain, traumatic nerve injury, recovery after traumatic brain injury, post-stroke pain, post-ischemia pain, fibromyalgia, chronic headache, migraine, tension-type headache, diabetic neuropathic pain, phantom limb pain, visceral pain and cutaneous pain.

Other aims of the present invention will become apparent to the skilled man directly from the foregoing and following remarks.

DETAILED DESCRIPTION

In a first aspect the present invention relates to compounds of general formula (I)

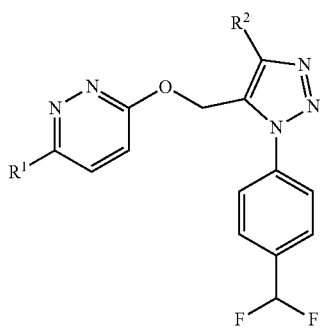

(I)

wherein
R$^1$ is selected from the group R$^{1a}$ consisting of
heteroaryl,
wherein the heteroaryl group is optionally substituted with 1 to 3 substituents independently selected from the group consisting of C$_{1-5}$-alkyl-, C$_{1-5}$-alkyl-O—, C$_{1-5}$-alkyl-C(O)—, C$_{1-5}$-alkyl-O—C(O)—, H(O)C—, HOOC—, C$_{3-6}$-cycloalkyl-, (R$^3$)$_2$N—, (R$^3$)$_2$N—C$_{1-5}$-alkyl-, (R$^3$)$_3$N$^+$—C$_{1-5}$-alkyl-, (R$^3$)$_2$N—C(O)—, NC—, HO—, oxo, C$_{1-5}$-alkyl-S(O)—, C$_{1-5}$-alkyl-S(O)$_2$—, halogen and imidazolyl, and
wherein the above mentioned C$_{1-5}$-alkyl-, C$_{1-5}$-alkyl-O—, C$_{1-5}$-alkyl-C(O)—, C$_{1-5}$-alkyl-O—C(O)—, C$_{3-6}$-cycloalkyl-, (R$^3$)$_2$N—, (R$^3$)$_2$N—C$_{1-5}$-alkyl-, (R$^3$)$_3$N$^+$—C$_{1-5}$-alkyl-, (R$^3$)$_2$N—C(O)—, C$_{1-5}$-alkyl-S(O)—, C$_{1-5}$-alkyl-S(O)$_2$— and imidazolyl groups are optionally substituted with 1 to 5 substituents independently selected from the group consisting of oxo, halogen, NC—, and HO—, and
wherein the heteroaryl group is a mono- or bicyclic-ring system containing one to three heteroatoms selected from N, O or S(O)$_r$, wherein r=0, 1 or 2, consisting of 5 to 10 ring atoms wherein at least one of the heteroatoms is part of an aromatic ring;
R$^2$ is selected from the group R$^{2a}$ consisting of
H—, halogen and C$_{1-3}$-alkyl-,
wherein the above mentioned C$_{1-3}$-alkyl-groups may optionally be substituted with 1 to 7 substituents independently from each other selected from the group consisting of halogen NC—, and HO—;
R$^3$ is selected from the group R$^{3a}$ consisting of
H— and C$_{1-3}$-alkyl-,
wherein the above mentioned C$_{1-3}$-alkyl-groups may optionally be substituted with 1 to 7 substituents independently from each other selected from the group consisting of halogen NC—, and HO—;
or a salt thereof.

Unless otherwise stated, the groups, residues, and substituents, particularly R$^1$, R$^2$, and R$^3$ are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
R$^1$ is selected from the group R$^{1b}$ consisting of
an aromatic monocyclic ring consisting of 5 or 6 ring atoms containing
one to three heteroatoms selected from N and O,
wherein the above mentioned aromatic monocyclic ring is optionally substituted with 1 to 3 substituents independently selected from the group consisting of C$_{1-5}$-alkyl-, C$_{1-5}$-alkyl-O—, C$_{1-5}$-alkyl-C(O)—, C$_{1-5}$-alkyl-O—C(O)—, H(O)C—, HOOC—, C$_{3-6}$-cycloalkyl-, (R$^3$)$_2$N—, (R$^3$)$_2$N—C$_{1-5}$-alkyl-, (R$^3$)$_2$N—C(O)—, NC—, HO—, oxo, C$_{1-5}$-alkyl-S(O)—, C$_{1-5}$-alkyl-S(O)$_2$-, halogen and imidazolyl, and
wherein the above mentioned C$_{1-5}$-alkyl-, C$_{1-5}$-alkyl-O—, C$_{1-5}$-alkyl-C(O)—, C$_{1-5}$-alkyl-O—C(O)—, C$_{3-6}$-cycloalkyl-, (R$^3$)$_2$N—, (R$^3$)$_2$N—C$_{1-5}$-alkyl-, (R$^3$)$_2$N—C(O)—, C$_{1-5}$-alkyl-S(O)—, C$_{1-5}$-alkyl-S(O)$_2$— and imidazolyl groups are optionally substituted with 1 to 5 substituents independently selected from the group consisting of oxo, halogen, NC—, and HO—.

In a further embodiment of the present invention
R$^1$ is selected from the group R$^{1c}$ consisting of
an aromatic monocyclic ring system containing one to three heteroatoms selected from N, O consisting of 5 to 6 ring atoms,
wherein the aromatic monocyclic ring system is optionally substituted with 1 to 3 substituents independently selected from the group consisting of C$_{1-5}$-alkyl-, C$_{1-5}$-alkyl-O—, C$_{3-6}$-cycloalkyl-, (R$^3$)$_2$N—C(O)—, NC— and halogen, and
wherein the above mentioned C$_{1-5}$-alkyl-, C$_{1-5}$-alkyl-O—, C$_{3-6}$-cycloalkyl- and (R$^3$)$_2$N—C(O)-groups are optionally substituted with 1 to 5 substituents independently selected from the group consisting of halogen and NC—.

In a further embodiment of the present invention R$^1$ is selected from the group R$^{1d}$ consisting of

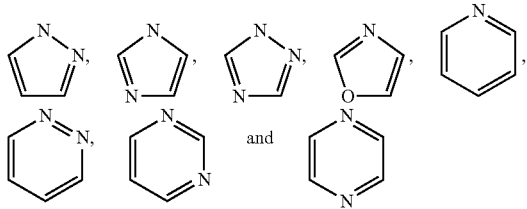

wherein the above aromatic monocyclic ring system is optionally substituted with 1 to 3 substituents independently selected from the group consisting of C$_{1-5}$-alkyl-, C$_{1-5}$-alkyl-O—, C$_{3-6}$-cycloalkyl-, (R$^3$)$_2$N—C(O)—, NC— and halogen, and wherein the above mentioned C$_{1-5}$-alkyl-, C$_{1-5}$-alkyl-O—, C$_{3-6}$-cycloalkyl- and (R$^3$)$_2$N—C(O)-groups are optionally substituted with 1 to 5 substituents independently selected from the group consisting of halogen and NC—.

In a further embodiment of the present invention R$^2$ is selected from the group R$^{2b}$ consisting of
C$_{1-3}$-alkyl-,
wherein the above mentioned C$_{1-3}$-alkyl-group may optionally be substituted with 1 to 7 substituents independently from each other selected from the group consisting of halogen NC—, and HO—.

In a further embodiment of the present invention R$^2$ is selected from the group R$^{2c}$ consisting of
H$_3$C—, FH$_2$C—, F$_2$HC— and F$_3$C—.

In a further embodiment of the present invention R$^2$ is selected from the group R$^{2d}$ consisting of
H$_3$C—.

In a further embodiment of the present invention R$^3$ is selected from the group R$^{3b}$ consisting of
H— and H$_3$C—.

Each R$^{1x}$, R$^{2x}$ and R$^{3x}$ represents a characterized, individual embodiment for the corresponding substituent as described above. Thus given the above definitions, individual embodiments of the first aspect of the invention are fully characterized by the term (R$^{1x}$, R$^{2x}$ and R$^{3x}$), wherein for each index x an individual figure is given that ranges from "a" to the highest letter given above. All individual embodiments described by the term in parentheses with full permutation of the indices x, referring to the definitions above, shall be comprised by the present invention.

The following Table 1 shows such embodiments E-1 to E-31 of the invention that are considered preferred. Embodiment E-31, represented by the entries in the last row of Table 1, is the most preferred embodiment.

TABLE 1

Embodiments E-1 to E-31 of the invention

| | R$^{1x}$ | R$^{2x}$ | R$^{3x}$ |
|---|---|---|---|
| E-1 | R$^{1a}$ | R$^{2a}$ | R$^{3b}$ |
| E-2 | R$^{1a}$ | R$^{2b}$ | R$^{3a}$ |
| E-3 | R$^{1a}$ | R$^{2b}$ | R$^{3b}$ |
| E-4 | R$^{1a}$ | R$^{2c}$ | R$^{3a}$ |
| E-5 | R$^{1a}$ | R$^{2c}$ | R$^{3b}$ |
| E-6 | R$^{1a}$ | R$^{2d}$ | R$^{3a}$ |
| E-7 | R$^{1a}$ | R$^{2d}$ | R$^{3b}$ |
| E-8 | R$^{1b}$ | R$^{2a}$ | R$^{3a}$ |

TABLE 1-continued

Embodiments E-1 to E-31 of the invention

| | R$^{1x}$ | R$^{2x}$ | R$^{3x}$ |
|---|---|---|---|
| E-9 | R$^{1b}$ | R$^{2a}$ | R$^{3b}$ |
| E-10 | R$^{1b}$ | R$^{2b}$ | R$^{3a}$ |
| E-11 | R$^{1b}$ | R$^{2b}$ | R$^{3b}$ |
| E-12 | R$^{1b}$ | R$^{2c}$ | R$^{3a}$ |
| E-13 | R$^{1b}$ | R$^{2c}$ | R$^{3b}$ |
| E-14 | R$^{1b}$ | R$^{2d}$ | R$^{3a}$ |
| E-15 | R$^{1b}$ | R$^{2d}$ | R$^{3b}$ |
| E-16 | R$^{1c}$ | R$^{2a}$ | R$^{3a}$ |
| E-17 | R$^{1c}$ | R$^{2a}$ | R$^{3b}$ |
| E-18 | R$^{1c}$ | R$^{2b}$ | R$^{3a}$ |
| E-19 | R$^{1c}$ | R$^{2b}$ | R$^{3b}$ |
| E-20 | R$^{1c}$ | R$^{2c}$ | R$^{3a}$ |
| E-21 | R$^{1c}$ | R$^{2c}$ | R$^{3b}$ |
| E-22 | R$^{1c}$ | R$^{2d}$ | R$^{3a}$ |
| E-23 | R$^{1c}$ | R$^{2d}$ | R$^{3b}$ |
| E-24 | R$^{1d}$ | R$^{2a}$ | R$^{3a}$ |
| E-25 | R$^{1d}$ | R$^{2a}$ | R$^{3b}$ |
| E-26 | R$^{1d}$ | R$^{2b}$ | R$^{3a}$ |
| E-27 | R$^{1d}$ | R$^{2b}$ | R$^{3b}$ |
| E-28 | R$^{1d}$ | R$^{2c}$ | R$^{3a}$ |
| E-29 | R$^{1d}$ | R$^{2c}$ | R$^{3b}$ |
| E-30 | R$^{1d}$ | R$^{2d}$ | R$^{3a}$ |
| E-31 | R$^{1d}$ | R$^{2d}$ | R$^{3b}$ |

Accordingly, for example E-5 covers compounds of formula (I),
wherein
R$^1$ is selected from the group R$^{1a}$ consisting of heteroaryl,
wherein the heteroaryl group is optionally substituted with 1 to 3 substituents independently selected from the group consisting of C$_{1-5}$-alkyl-, C$_{1-5}$-alkyl-O—, C$_{1-5}$-alkyl-C(O)—, C$_{1-5}$-alkyl-O—C(O)—, H(O)C—, HOOC—, C$_{3-6}$-cycloalkyl-, (R$^3$)$_2$N—, (R$^3$)$_2$N—C$_{1-5}$-alkyl-, (R$^3$)$_2$N—C(O)—, NC—, HO—, oxo, C$_{1-5}$-alkyl-S(O)—, C$_{1-5}$-alkyl-S(O)$_2$—, halogen and imidazolyl, and
wherein the above mentioned C$_{1-5}$-alkyl-, C$_{1-5}$-alkyl-O—, C$_{1-5}$-alkyl-C(O)—, C$_{1-5}$-alkyl-O—C(O)—, C$_{3-6}$-cycloalkyl-, (R$^3$)$_2$N—, (R$^3$)$_2$N—C$_{1-5}$-alkyl-, (R$^3$)$_2$N—C(O)—, C$_{1-5}$-alkyl-S(O)—, C$_{1-5}$-alkyl-S(O)$_2$— and imidazolyl groups are optionally substituted with 1 to 5 substituents independently selected from the group consisting of oxo, halogen, NC—, and HO—, and
wherein the heteroaryl group is a mono- or bicyclic-ring system containing one to three heteroatoms selected from N, O or S(O)$_r$, wherein r=0, 1 or 2, consisting of 5 to 10 ring atoms wherein at least one of the heteroatoms is part of an aromatic ring;
R$^2$ is selected from the group R$^{2C}$ consisting of
H$_3$C—, FH$_2$C—, F$_2$HC— and F$_3$C—;
R$^3$ is selected from the group R$^{3b}$ consisting of
H— and H$_3$C—;
or a salt thereof.

Accordingly, for example E-15 covers compounds of formula (I),
wherein
R$^1$ is selected from the group R$^{1b}$ consisting of
an aromatic monocyclic ring consisting of 5 or 6 ring atoms containing one to three heteroatoms selected from N and O,
wherein the above mentioned aromatic monocyclic ring is optionally substituted with 1 to 3 substituents independently selected from the group consisting of C$_{1-5}$-alkyl-, C$_{1-5}$-alkyl-O—, C$_{1-5}$-alkyl- C(O)—, C$_{1-5}$-alkyl-O—C(O)—, H(O)C—, HOOC—, C$_{3-6}$-cycloalkyl-, (R$^3$)$_2$N—, (R$^3$)$_2$N—C$_{1-5}$-alkyl-, (R$^3$)$_2$N—C(O)—, NC—, HO—, oxo, C$_{1-5}$-alkyl-S(O)—, C$_{1-5}$-alkyl-S(O)$_2$-, halogen and imidazolyl, and wherein the above mentioned C$_{1-5}$-alkyl-, C$_{1-5}$-alkyl-O—, C$_{1-5}$-alkyl-C(O)—, C$_{1-5}$-alkyl-O—C(O)—, C$_{3-6}$-cycloalkyl-, (R$^3$)$_2$N—, (R$^3$)$_2$N—C$_{1-5}$-alkyl-, (R$^3$)$_2$N—C(O)—, C$_{1-5}$-alkyl-S(O)—, C$_{1-5}$-alkyl-S(O)$_2$— and imidazolyl groups are optionally substituted with 1 to 5 substituents independently selected from the group consisting of oxo, halogen, NC—, and HO—;

R$^2$ is selected from the group R$^{2d}$ consisting of
    H$_3$C—;
R$^3$ is selected from the group R$^{3b}$ consisting of
    H— and H$_3$C—;
or a salt thereof.

Further preferred are the following compounds listed in Table 2:

| Example | Structure |
|---|---|
| 1 | |
| 2 | |
| 3 | |
| 4 | 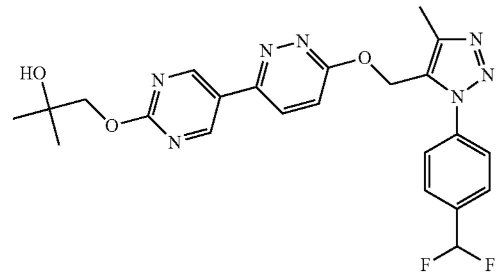 [SMILES: Cc1nnn(-c2ccc(C(F)F)cc2)c1COc1ccc(-c2cnc(OCC(C)(C)O)nc2)nn1] |
| 5 | 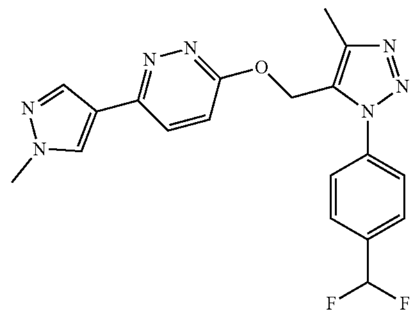 [SMILES: Cc1nnn(-c2ccc(C(F)F)cc2)c1COc1ccc(-c2cnn(C)c2)nn1] |
| 6 | 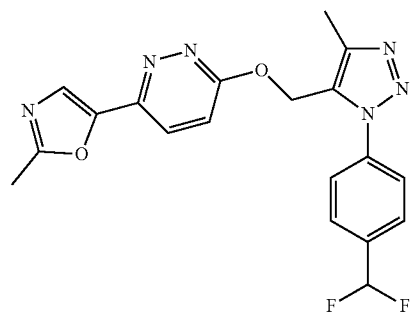 [SMILES: Cc1ncc(-c2ccc(OCc3c(C)nnn3-c3ccc(C(F)F)cc3)nn2)o1] |
| 7 | 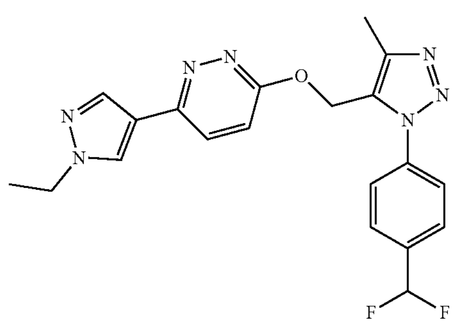 [SMILES: CCn1cc(-c2ccc(OCc3c(C)nnn3-c3ccc(C(F)F)cc3)nn2)cn1] |
| 8 | 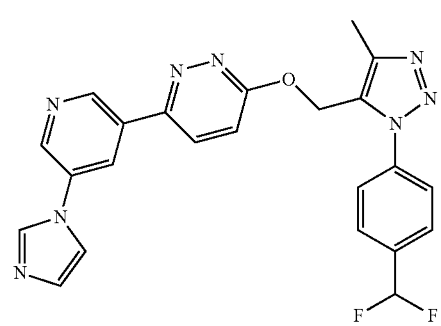 [SMILES: Cc1nnn(-c2ccc(C(F)F)cc2)c1COc1ccc(-c2cncc(-n3ccnc3)c2)nn1] |

| Example | Structure |
|---|---|
| 9 | 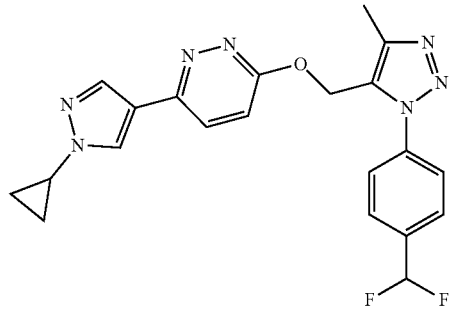 [SMILES: Cc1nnn(-c2ccc(C(F)F)cc2)c1COc1ccc(-c2cnn(C3CC3)c2)nn1] |
| 10 | 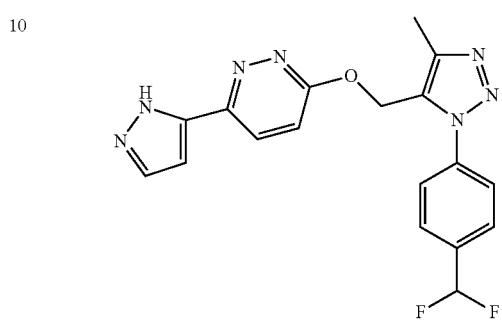 |
| 11 | 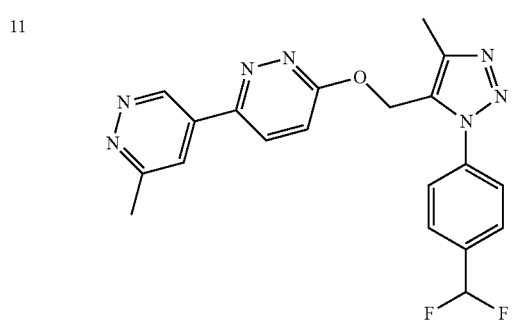 |
| 12 | 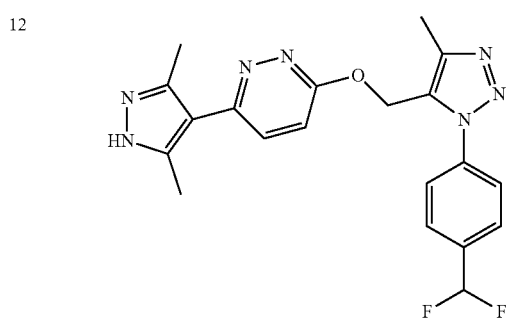 |
| 13 | 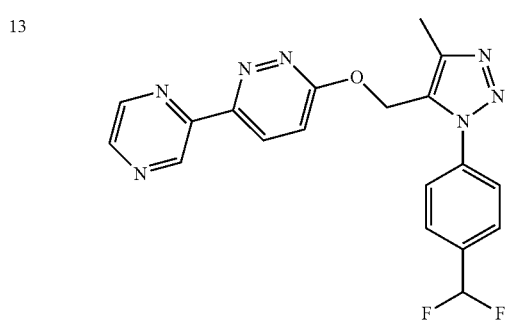 |
| 14 | 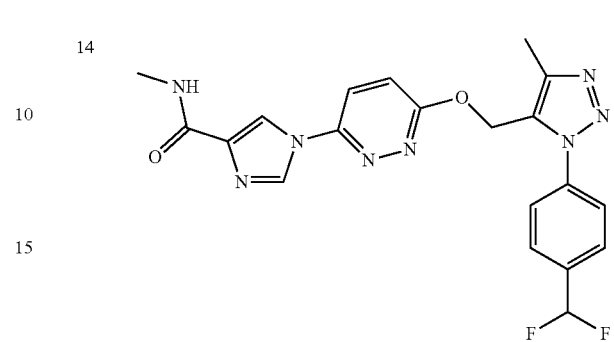 |
| 15 | 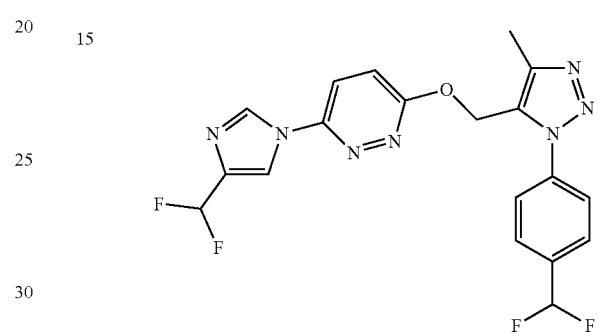 |
| 16 | 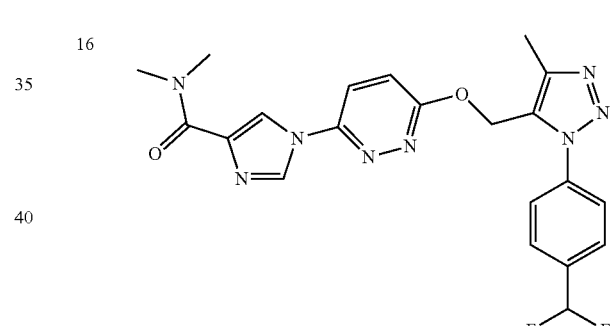 |
| 17 | 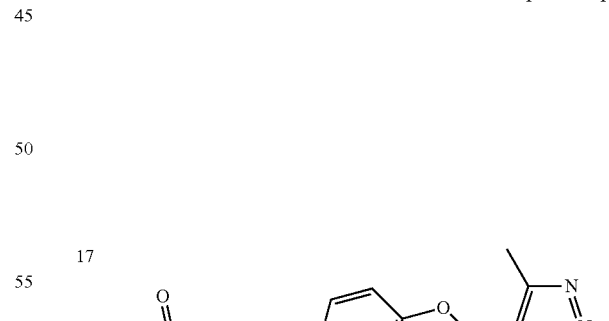 |

| Example | Structure |
|---|---|
| 18 | 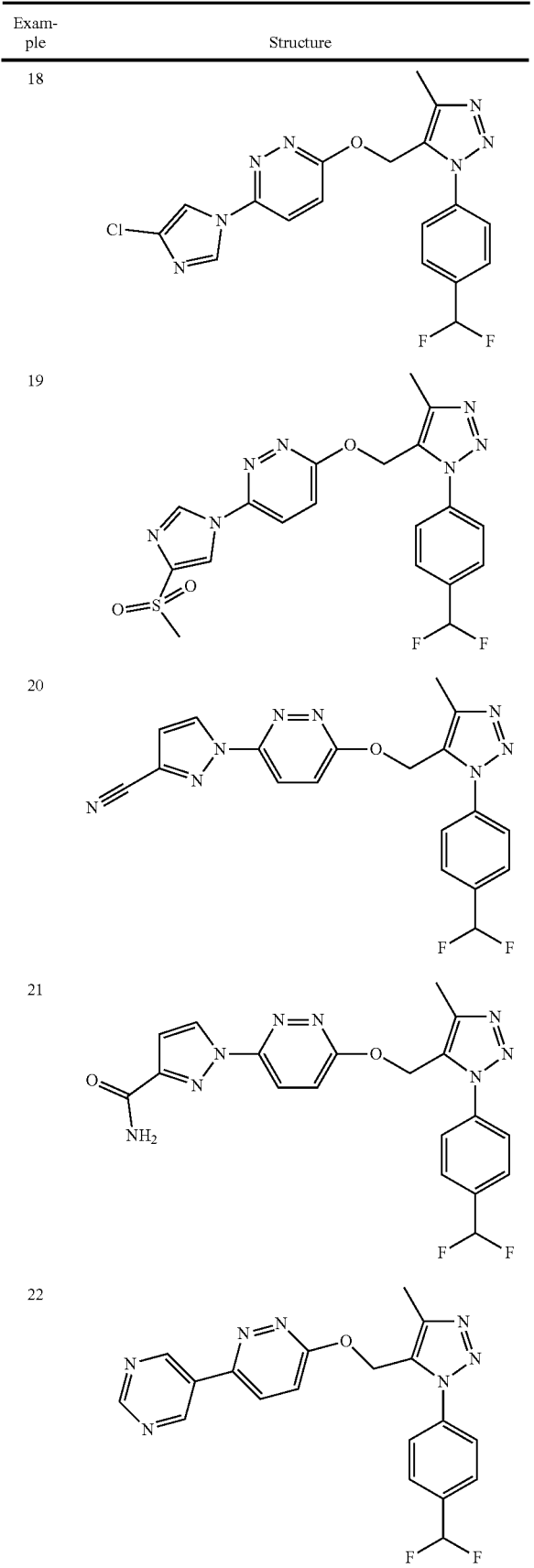 |
| 19 | |
| 20 | |
| 21 | |
| 22 | |
| Example | Structure |
|---|---|
| 23 | 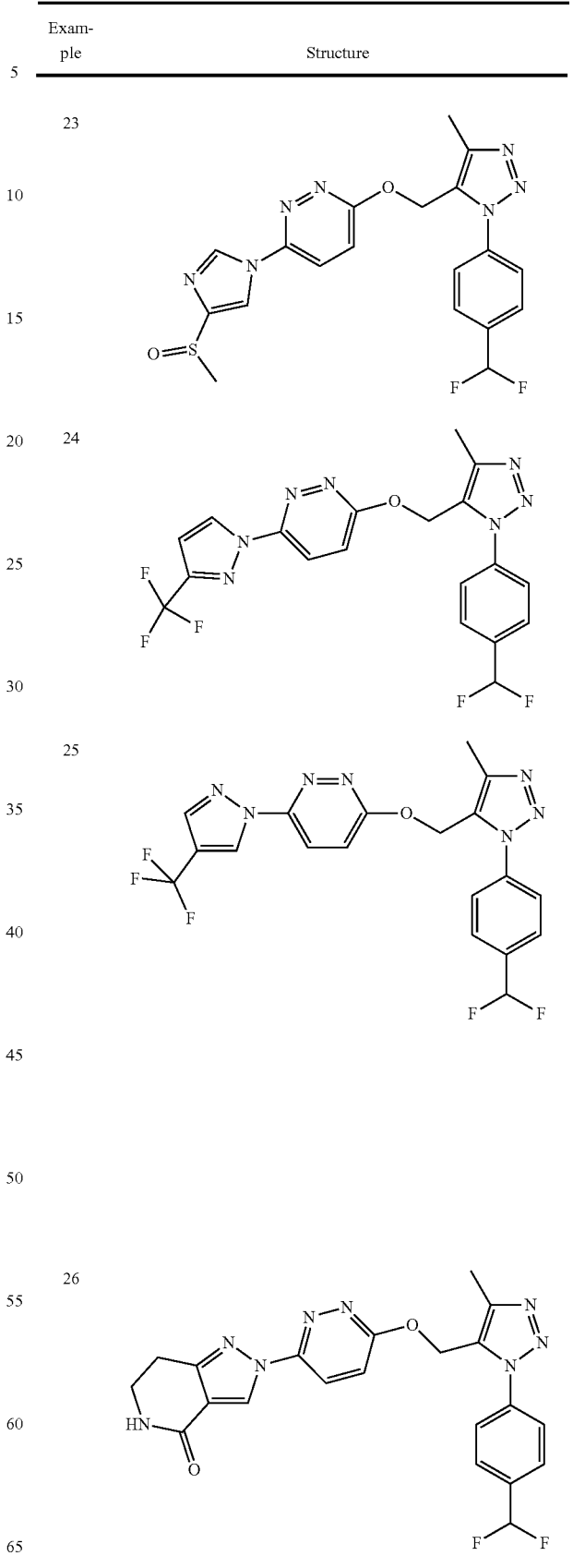 |
| 24 | |
| 25 | |
| 26 | |

TABLE-continued
| Example | Structure |
|---|---|
| 27 | 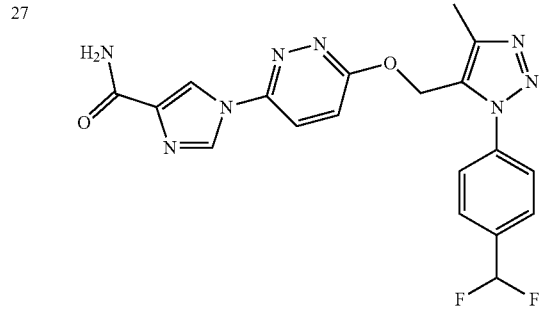 |
| 28 | 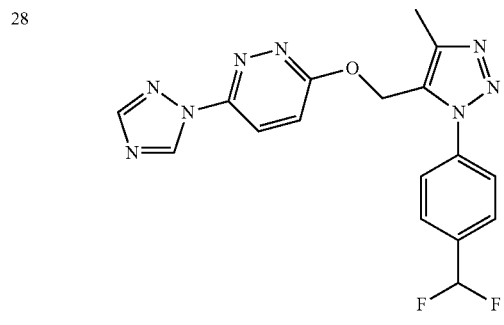 |
| 29 | 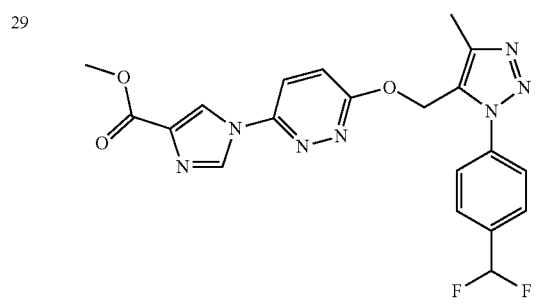 |
| 30 | 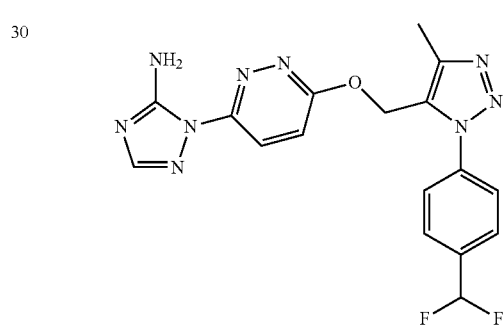 |
| 31 | 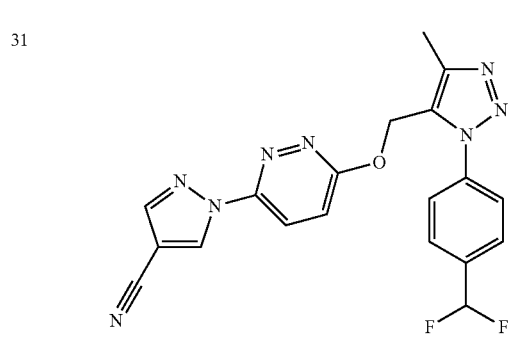 |
| 32 | 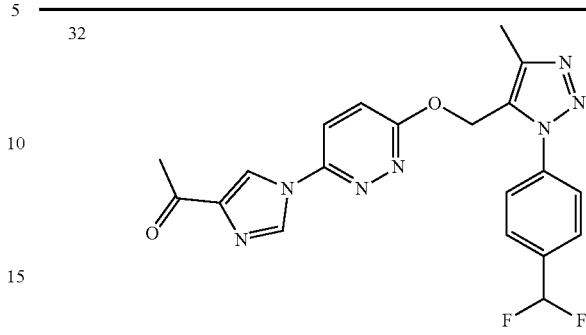 |
| 33 | 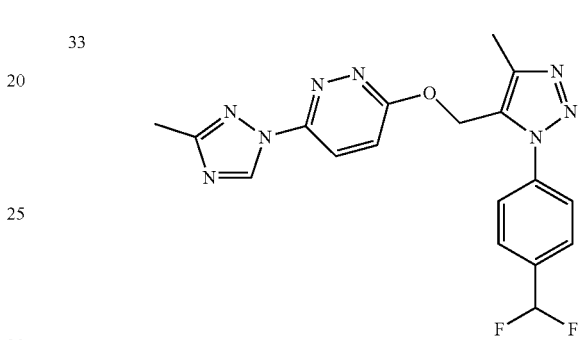 |
| 34 | 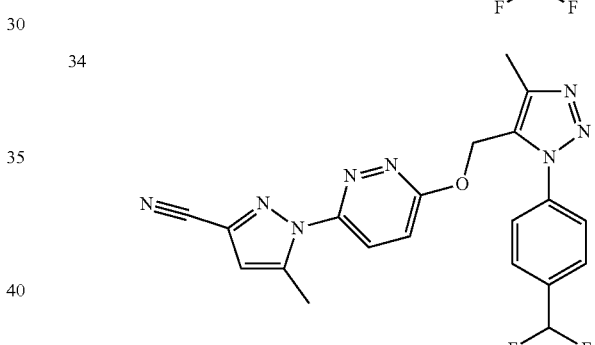 |
| 35 |  |
| 35 | 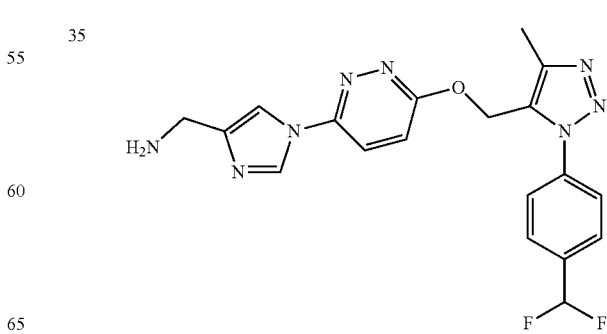 |

-continued

| Example | Structure |
|---|---|
| 36 | (structure) |
| 37 | (structure) |
| 38 | (structure) |
| 39 | (structure) |
| 40 | (structure) | or the salts thereof.

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO—, $H_2N$—, (O)S—, $(O)_2S$—, NC— (cyano), HOOC—, $F_3C$— or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In general, the attachment site of a given residue to another group shall be variable, i.e. any capable atom, bearing hydrogens to be replaced, within this residue may be the linking spot to the group being attached, unless otherwise indicated.

In case a compound of the present invention is depicted in form of a chemical name and as a formula in case of any discrepancy the formula shall prevail.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" or "physiologically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoro acetate salts,) also comprise a part of the invention.

The term "substituted" as used herein means that any one or more hydrogens on the designated atom is replaced with a selection from the indicated group, provided that the designated atom's viable valence number is not exceeded, and that the substitution results in a stable compound.

The term "partially unsaturated" as used herein means that in the designated group or moiety 1, 2, or more, preferably 1 or 2, double bonds are present. Preferably, as used herein, the term "partially unsaturated" does not cover fully unsaturated groups or moieties.

The term "halogen" generally denotes fluorine (F), chlorine (Cl), bromine (Br) and iodine (I).

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means a mono- or bicyclic-ring systems containing one to three heteroatoms selected from N, O or $S(O)_r$, wherein r=0, 1 or 2, consisting of 5 to 10 ring atoms wherein at least one of the heteroatoms is part of an aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

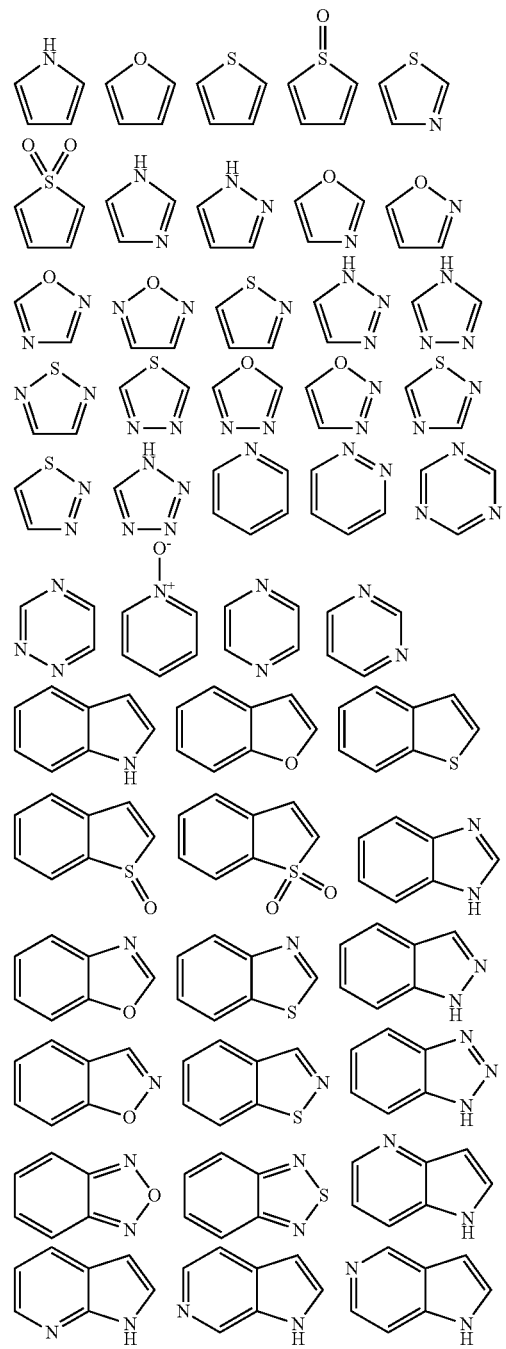

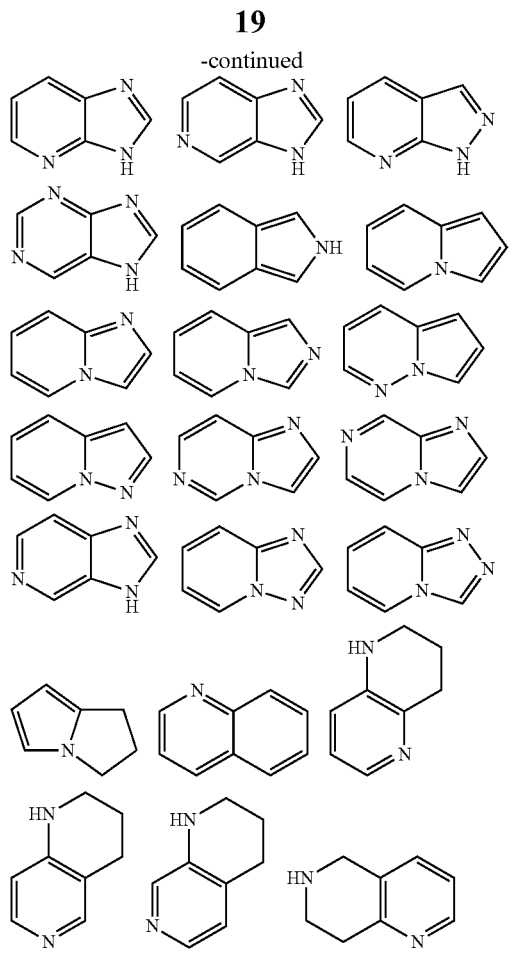

Many of the terms given above may be used repeatedly in the definition of a formula or group and in each case have one of the meanings given above, independently of one another.

The compounds according to the invention may be obtained using methods of synthesis known in principle. Preferably, the compounds are obtained by the following methods according to the invention which are described in more detail hereinafter.

The intermediate {1-[4-(difluoromethyl)phenyl]-4-methyl-1H-1,2,3-triazol-5-yl}methanol has been synthesized according to two different routes:

Route 1

After the formation of the tosylhydrazone under the standard conditions, the aniline is added and conducts a nucleophilic attack on the tosylhydrazone, followed by intramolecular cyclization and aromatization which leads to the formation of the desired triazole. The triazole is deprotonated by a strong base and the corresponding anion is trapped by paraformaldehyde to afford alcohol I.

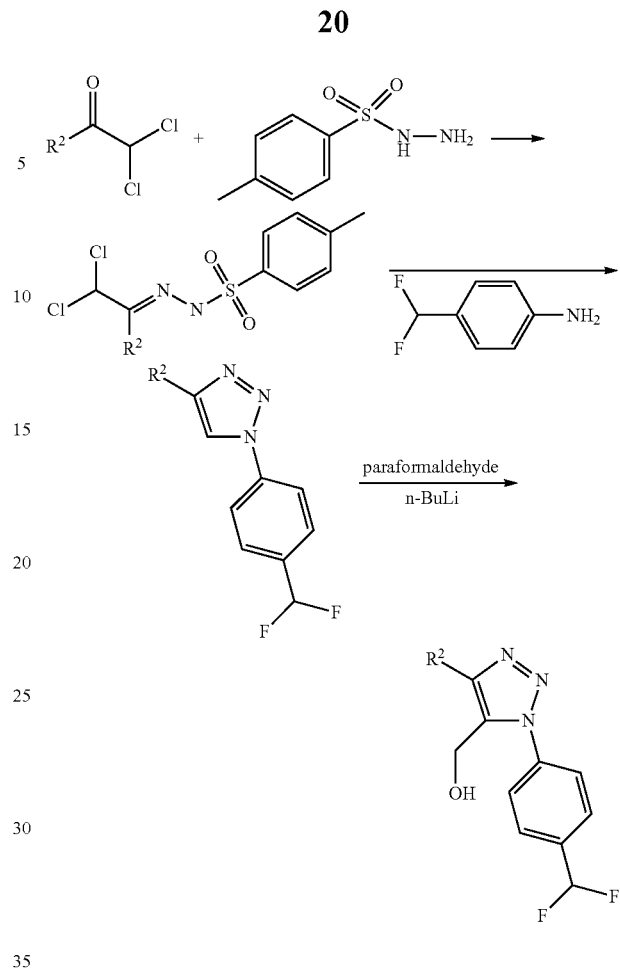

Route 2

After the formation of the tosylhydrazone under standard conditions, the aniline is added and conducts a nucleophilic attack on the tosylhydrazone, followed by intramolecular cyclization and aromatization which leads to the formation of the esther-triazole. The esther-triazole is then reduced to afford the corresponding alcohol I.

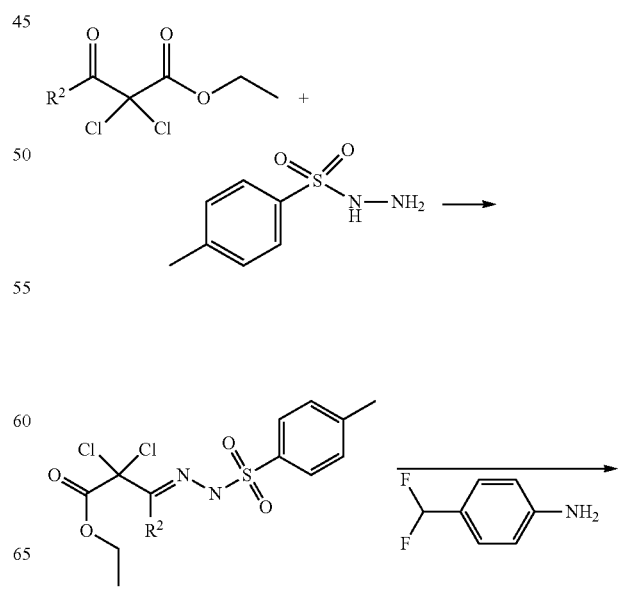

-continued

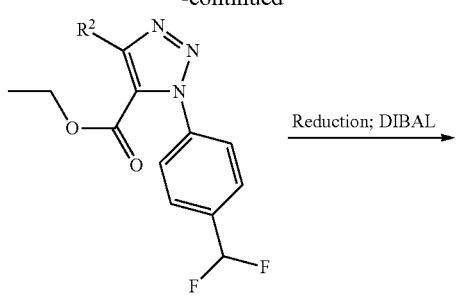

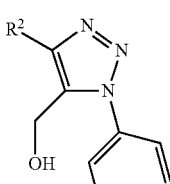

Starting from {1-[4-(difluoromethyl)phenyl]-4-methyl-1H-1,2,3-triazol-5-yl}methanol the final molecules have been synthesized either by route 3 or by route 4.

Route 3

{1-[4-(difluoromethyl)phenyl]-4-methyl-1H-1,2,3-triazol-5-yl}methanol is treated with 3,6-dichloropyridazine to form a corresponding chloride, which is further functionalised via the Suzuki coupling, Buchwald coupling or aromatic nucleophilic substitution to provide the desired product.

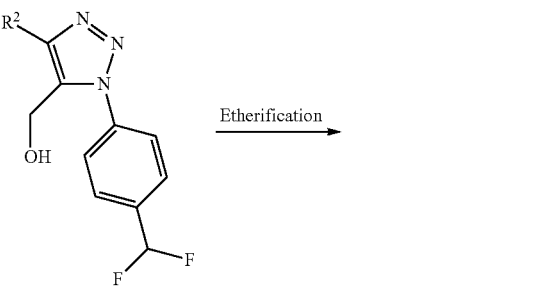

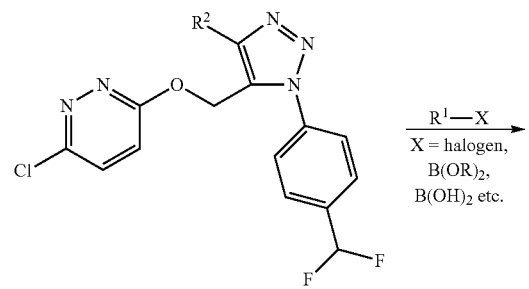

-continued

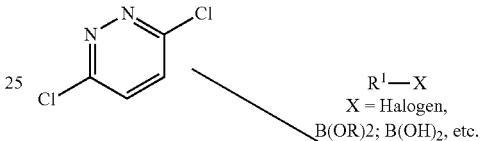

Route 4

The synthesis starts with the formation of a chloro intermediate using 3,6-dichloropyridazine via either the Suzuki coupling, Buchwald coupling or aromatic nucleophilic. Subsequent coupling with {1-[4-(difluoromethyl)phenyl]-4-methyl-1H-1,2,3-triazol-5-yl}methanol under standard conditions provides the desired product.

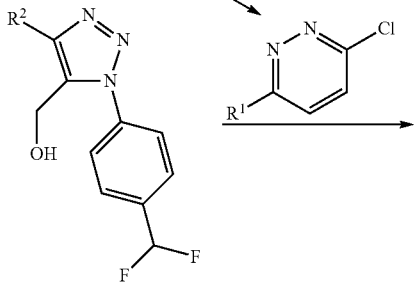

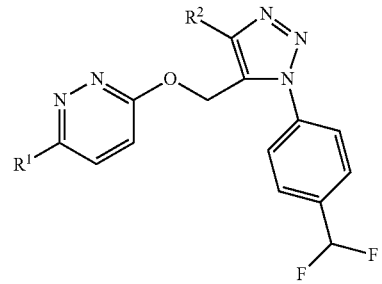

The Examples that follow are intended to illustrate the present invention without restricting it. The terms "ambient temperature" and "room temperature" are used interchangeably and designate a temperature of about 20° C.

Abbreviations

| | |
|---|---|
| ACN | acetonitrile |
| AcOH | acetic acid |
| Aq. | aqueous |
| ° C. | Degree celsius |
| CH | cyclohexane |
| Conc. | concentrated |
| DAST | diethylaminosulfur trifluoride |
| DCC | N,N'-Dicyclohexylcarbodiimid |
| DCM | dichloro methane |
| DIPE | diisopropyl ether |

| | |
|---|---|
| DIPEA | N,N-diisopropylethylamine |
| DMF | N,N-dimethylformamide |
| DMSO | dimethyl sulfoxide |
| dppf | 1,1'-Ferrocenediyl-bis(diphenylphosphine) |
| ESI-MS | Electrospray ionisation mass spectrometry |
| EtOAc/EE | ethyl acetate |
| EtOH | ethanol |
| Et$_2$O | diethyl ether |
| Ex | example |
| Eq | equivalent |
| h | hour |
| HATU | N,N,N',N'-tetramethyl-O-(7-azabenzotriazol-1-yl)uranium hexafluorophosphate |
| HCl | Hydrochlorid acid |
| HPLC | High performance liquid chromatography |
| HCOOH | formic acid |
| L | liter |
| MeOH | methanol |
| NaHCO$_3$ | sodium bicarbonate |
| min | minute |
| mL | milliliter |
| MTBE | tert-butylmethylether |
| NaH | Sodium hydride |
| o/n | overnight |
| Pd/C | palladium on activated carbon |
| Pd$_2$(dba)$_3$ | Tris(dibenzylideneacetone)dipalladium(II) |
| Pd-PEPPSI | [1,3-Bis[2,6-bis(1-ethylpropyl)phenyl]-4,5-dichloro-imidazol-2-yl]-dichloro-(2-methyl-1-pyridyl)palladium |
| PE | petroleum ether |
| Ra-Ni | Raney Nickel |
| RT | room temperature (about 20° C.) |
| sat. | saturated |
| TBTU | Benzotriazolyl tetramethyluronium tetrafluoroborate |
| TEA | triethylamine |
| Tetrakis | Tetrakis(triphenylphosphin)-palladium(0) |
| TFA | trifluoroacetic acid |
| THF | tetrahydrofuran |
| TLC | Thin-layer chromatography on SiO$_2$ |
| XPhos | 2-Dicyclohexylphosphino-2',4',6'-triisopropylbiphenyl |

Analytical HPLC Methods

| Method A | | | |
|---|---|---|---|
| time (min) | Vol % water (incl. 0.1% TFA) | Vol % ACN | Flow [mL/min] |
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire (Waters) 2.5 μm; 3.0 × 30 mm; column temperature: 60° C.

| Method B | | | |
|---|---|---|---|
| time (min) | Vol % water (incl. 0.1% TFA) | Vol % ACN (incl. 0.08% TFA) | Flow [mL/min] |
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: Sunfire C18 (Waters) 2.5 μm; 3.0 × 30 mm; column temperature: 60° C.

| Method C | | | |
|---|---|---|---|
| time (min) | Vol % water (incl. 0.1% NH$_4$OH) | Vol % ACN | Flow [mL/min] |
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: XBridge C18 (Waters) 2.5 μm; 3.0 × 30 mm; column temperature: 60° C.

| Method D | | | |
|---|---|---|---|
| time (min) | Vol % water (incl. 0.1% NH$_3$) | Vol % ACN | Flow [mL/min] |
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: XBridge C18 (Waters) 2.5 μm; 3.0 × 30 mm; column temperature: 60° C.

| Method E | | | |
|---|---|---|---|
| time (min) | Vol % water (incl. 0.1% TFA) | Vol % ACN (incl. 0.08% TFA) | Flow [mL/min] |
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: Sunfire C18 (Waters) 2.5 μm; 3.0 × 30 mm; column temperature: 60° C.

| Method F | | | |
|---|---|---|---|
| time (min) | Vol % water (incl. 0.1% TFA) | Vol % ACN (incl. 0.08% TFA) | Flow [mL/min] |
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: Sunfire C18 (Waters) 2.5 μm; 3.0 × 30 mm; column temperature: 60° C.

| Method G | | | |
|---|---|---|---|
| time (min) | Vol % water (incl. 0.1% NH$_4$OH) | Vol % ACN | Flow [mL/min] |
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: XBridge C18 (Waters) 2.5 μm; 3.0 × 30 mm; column temperature: 60° C.

Method H

| time (min) | Vol % water (incl. 0.1% NH₃) | Vol % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: XBridge C18 (Waters) 2.5 μm; 3.0 × 30 mm; column temperature: 60° C.

Method I

| time (min) | Vol % water (incl. 0.1% TFA) | Vol % ACN | Flow [mL/min] |
|---|---|---|---|
| 0.00 | 99 | 1 | 1.3 |
| 0.02 | 99 | 1 | 1.3 |
| 1.0 | 0 | 100 | 1.3 |
| 1.1 | 0 | 100 | 1.3 |
| 1.15 | 99 | 1 | 1.3 |
| 2.0 | 99 | 1 | 1.3 |

Analytical column: Sunfire C18 2.5 μm 2.1 × 30 mm; column temperature: 60° C.

Method J

| time (min) | Vol % water (incl. 0.1% TFA) | Vol % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |

Analytical column: Sunfire C18 2.5 μm; 3.0 × 30 mm; column temperature: 60° C.

Method K

| time (min) | Vol % [H₂O 0.1% NH₄OH] | Vol % [Acetonitrile] | Flow [ml/min] |
|---|---|---|---|
| 0.0 | 97 | 3 | 2.2 |
| 0.2 | 97 | 3 | 2.2 |
| 1.2 | 0 | 100 | 2.2 |
| 1.25 | 0 | 100 | 3.0 |
| 1.4 | 0 | 100 | 3.0 |

Analytical column: XBridge C18_3.0 × 30 mm, 2.5 μm; column temperature: 60° C.

Method L

| Gradient/Solvent Time [min] | Vol % [H₂O, 0.1% TFA] | Vol % [Acetonitril] | Flow [ml/min] |
|---|---|---|---|
| 0.0 | 99 | 1 | 1.6 |
| 0.02 | 99 | 1 | 1.6 |
| 1.00 | 0 | 100 | 1.6 |
| 1.10 | 0 | 100 | 1.6 |

Analytical column: Xbridge BEH C18, 2.1×30 mm, 1.7 μm; column temperature: 60° C.

Preparation of Starting Compounds

Example I—Route 1 in the General Scheme

{1-[4-(difluoromethyl)phenyl]-4-methyl-1H-1,2,3-triazol-5-yl}methanol

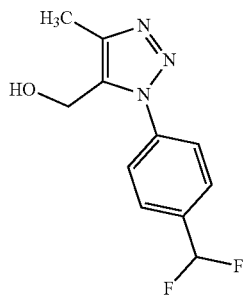 [SMILES: Cc1nnn(-c2ccc(C(F)F)cc2)c1CO]

Example I.1

N'-[1,1-dichloropropan-2-ylidene]-4-methylbenzene-1-sulfonohydrazide

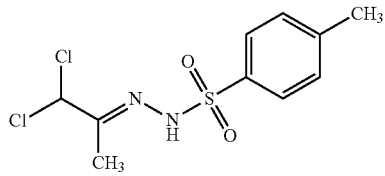 [SMILES: C/C(=N\NS(=O)(=O)c1ccc(C)cc1)C(Cl)Cl]

E/Z Configuration Unknown

To a suspension of p-toluenesulfonhydrazide (150.0 g, 781.3 mmol) in iPrOH (3.00 L) and acetic acid (22.4 mL, 391 mmol) 1,1-dichloroacteone (79.6 mL, 820 mmol) is added dropwise within 25 min at room temperature. The dropping funnel is flushed with cyclohexane (20 mL) and the suspension is diluted with iPrOH (500 mL). After stirring for 18 h, the suspension is filtered and washed with cyclohexane (250 mL). The isolated solid is dried at 40° C. to yield 187 g of the product. The compound is not characterized by MS and use in the next steps without further any purification

Example I.2

4-(difluoromethyl)aniline hydrochloride

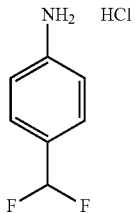

To 1-difluoromethyl-4-nitrobenzene (50.0 g, 288.8 mmol) in ethyl acetate (250 mL) palladium on carbon (10%, 0.5 g) is added. The reaction mixture is stirred under an atmosphere of hydrogen (1 bar) for 22 h at 00° C. The mixture is filtered and washed with ethyl acetate (50 mL). HCl in dioxane (80 mL, 4 mol/L, 320 mmol) is added dropwise within 20 min to the filtrate. The resulted suspension is stirred for 30 min at 0° C. and then filtered and washed with ethyl acetate (50 mL). The isolated solid is dried at 30° C. to yield 44.0 g of the product.

ESI-MS: 144.070 [M+H]+ very small signal.

$^1$H NMR (400 MHz, DMSO-$d_6$) δ=7.79-7.64 (m, 2H), 7.62-7.51 (m, 2H), 7.26-6.89 (t, J=55.6 Hz, 1H)—NH$_2$ not visible in the spectrum.

Example I.3

1-[4-(difluoromethyl)phenyl]-4-methyl-1H-1,2,3-triazole

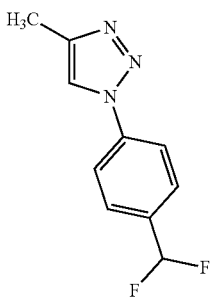

To a suspension of 4-(difluoromethyl)aniline hydrochloride (Example I.2, 5.0 g, 27.8 mmol) and N'-[1,1-dichloropropan-2-ylidene]-4-methylbenzene-1-sulfonohydrazide (8.2 g, 27.8 mmol) in acetonitrile (23.75 mL) and water (1.25 mL) pyridine (7.0 mL, 86.7 mmol) is added dropwise within 12 min at 5° C. The mixture is stirred for 2 h at 0° C. and is then warmed to 20° C. within 1 h. After 4 h water (30 mL) is added and the mixture is cooled to 5° C.

After stirring for 35 min, the suspension is filtered and washed with a cold mixture of acetonitrile (5 mL) and water and (10 mL). The isolated solid is dried at 40° C. to yield 4.1 g of the product.

ESI-MS: 210.110 [M+H]$^+$ $^1$H NMR (400 MHz, DMSO-$d_6$) δ=8.61 (s, 1H), 8.11-7.94 (m, 2H), 7.79 (d, J=8.6 Hz, 2H), 7.38-6.82 (m, 1H), 2.34 (s, 3H)

Example I

{1-[4-(difluoromethyl)phenyl]-4-methyl-1H-1,2,3-triazol-5-yl}methanol

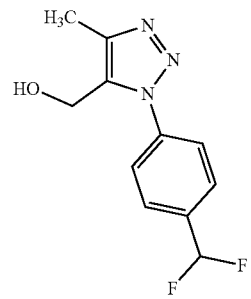 [SMILES: Cc1nnn(-c2ccc(C(F)F)cc2)c1CO]

To a suspension of 1-[4-(difluoromethyl)phenyl]-4-methyl-1H-1,2,3-triazole (Example I.3, 15.8 g, 75.5 mmol) in dry THF in a flask with a stir bar (300 mL) n-BuLi in hexane (51.4 mL, 128.4 mmol, 2.5 M) is added dropwise within 30 min at −70° C. After 40 min paraformaldehyde (13.6 g, 151.1 mmol) is added and the cooling bath is removed. After 19 h at room temperature, the reaction mixture is added to a mixture of water (100 mL) and ethyl acetate (200 mL). The organic layer is concentrated in vacuo.

The crude product is purified by flash column chromatography on silica gel to provide 12.8 g of the product.

ESI-MS: 240.050 [M+H]+

$^1$H NMR (400 MHz, DMSO-$d_6$) δ=8.00-7.68 (m, 5H), 7.35-6.92 (t, J=55.5 Hz, 1H), 5.53 (t, J=5.4 Hz, 1H), 4.52 (d, J=5.3 Hz, 1H), 4.59-4.41 (m, 1H), 2.35 (s, 4H)

Example I—Alternative Route 2 in the General Scheme

Example I.4

Ethyl-2,2-dichloro-3-[(4-methylbenzenesulfonamido)imino]butanoate

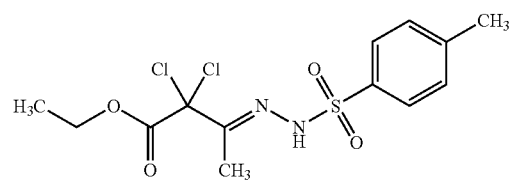 [SMILES: CCOC(=O)C(Cl)(Cl)/C(C)=N/NS(=O)(=O)c1ccc(C)cc1]

E/Z Configuration Unknown

To a suspension of p-toluenesulfonhydrazide (25.0 g, 134.2 mmol) in iPrOH (100 mL) ethyl 2,2-dichloro-3 oxobutanoate (21.3 mL, 141.0 mmol) is added dropwise. After seeding with product and stirring at 20° C. for 2.5 h, the suspension is cooled to 00° C. (1 h) and then filtered. The isolated solid is dried to yield 39.5 g of the product. The compound is used is the next step without any further purification.

Example I.5

Ethyl 1-[4-(difluoromethyl)phenyl]-4-methyl-1H-1,2,3-triazole-5-carboxylate

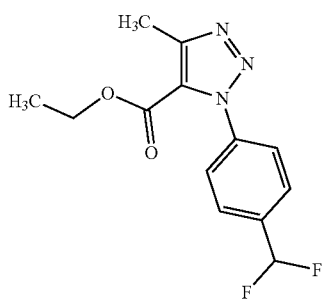 [SMILES: CCOC(=O)c1c(C)nnn1-c1ccc(C(F)F)cc1]

To a suspension of 4-(difluoromethyl)aniline hydrochloride (Example I.2, 10.0 g, 55.5 mmol) and ethyl 2,2-dichloro-3-[(4-methylbenzenesulfonamido)imino]butanoate (Example I.4, 21.0 g, 57.0 mmol) in iPrOH (400 mL), triethylamine (32.0 mL, 230.0 mmol) is added under ice cooling. The mixture is stirred for 22 h at room temperature. The orange suspension is filtered and the filtrate concentrated in vacuo. The residue is dissolved in ethyl acetate (200 mL). The solution is washed three times with 1 M aqueous HCl (100 mL each). The organic layer is dried over Na$_2$SO$_4$ and concentrated after filtration. The residue is mixed with silica gel (20 g) and methyl cyclohexane (480 mL). After refluxing for 1 h, the hot suspension is filtered, and the filtrate is concentrated to a yellow suspension. The suspension is cooled to 0° C. The suspension is filtered and the isolated solid is dried at 40° C. to yield 12.2 g of the product.

ESI-MS: 282.090 [M+H]+
$^1$H NMR (400 MHz, DMSO-d$_6$) δ=7.86-7.60 (m, 4H), 7.33-6.98 (t, J=56.0 Hz, 1H), 4.20 (q, J=7.1 Hz, 2H), 2.54 (s, 3H), 1.13 (t, J=7.2 Hz, 3H)

Example I

{1-[4-(difluoromethyl)phenyl]-4-methyl-1H-1,2,3-triazol-5-yl}methanol

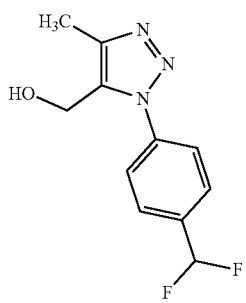 [SMILES: Cc1nnn(-c2ccc(C(F)F)cc2)c1CO]

To a cooled (ice bath) solution of ethyl 1-[4-(difluoromethyl)phenyl]-4-methyl-1H-1,2,3-triazole-5-carboxylate (15.5 g, 55.1 mmol) in dry THF (300 mL), 1M DIBAL in CH$_2$Cl$_2$ (121 mL, 121.0 mmol) is added dropwise during 1 h. The reaction mixture is stirred for 21.5 h at room temperature. Water (1 mL) is added and the suspension is concentrated in vacuo. The residue is treated with ethyl acetate (300 mL) and the resulted mixture is washed three times with 1M aqueous HCl (100 mL each). The organic layer is dried over Na$_2$SO$_4$ and filtered. The filtrate is evaporated in vacuo to dryness to yield 12 g of product.

ESI-MS: 240.050 [M+H]+
$^1$H NMR (400 MHz, DMSO-d$_6$) δ=8.00-7.68 (m, 5H), 7.35-6.92 (t, J=55.5 Hz, 1H), 5.53 (t, J=5.4 Hz, 1H), 4.52 (d, J=5.3 Hz, 1H), 4.59-4.41 (m, 1H), 2.35 (s, 4H)

Example II 3-chloro-6-[4-(difluoromethyl)-1H-imidazol-1-yl]pyridazine

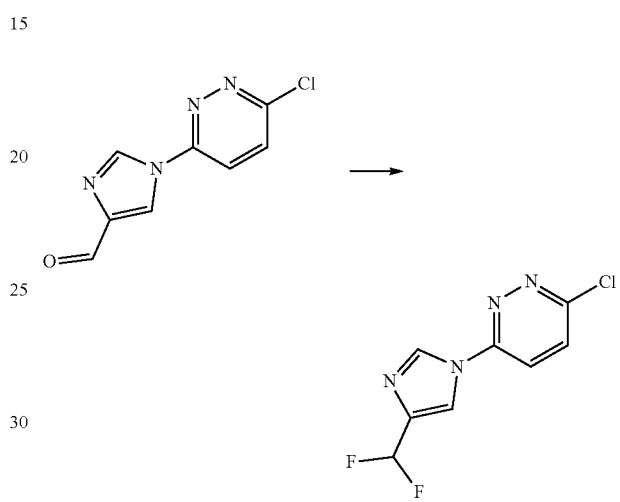

To 1-(6-chloropyridazin-3-yl)-1H-imidazole-4-carbaldehyde (Example VII.1, 2.1 g, 0.01 mol) in 200 ml DCM is added diethylaminosulfur trifluoride (4.2 ml, 0.03 mol) dropwise under ice bath cooling. The mixture is stirred for 4 days at RT, quenched with ice-water under ice-water bath cooling and neutralized with aq. NaHCO$_3$. The aqueous phase is extracted with DCM. The organic phase is dried over Na$_2$SO$_4$ and the solvent is removed. The residue is purified by silica column to yield to 1.2 g of the product.

C$_6$H$_4$BrF$_2$N (M=231.00 g/mol)
ESI-MS: 232 [M+H]$^+$
R$_t$ (HPLC): 0.69 min (Method K)

Example III.1

3-chloro-6-({1-[4-(difluoromethyl)phenyl]-4-methyl-1H-1,2,3-triazol-5-yl}methoxy)pyridazine

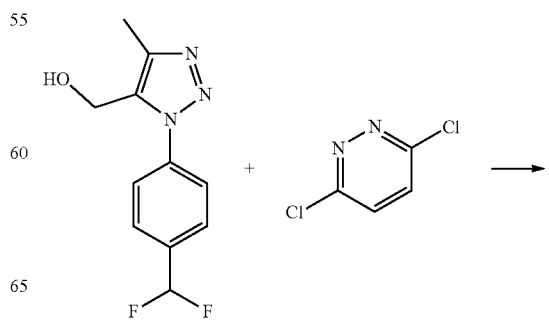

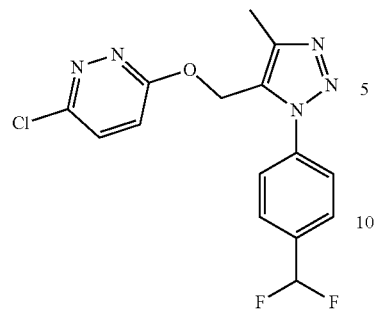

To Example I (1.00 g, 4.18 mmol) in 2 mL THF is added sodium hydride (273 mg, 6.27 mmol) under ice cooling. The reaction mixture is stirred at 00° C. for 30 min, then a solution of 3,6-dichloropyridazine (934 mg, 6.27 mmol) in 2 mL THF is added and stirred at RT o/n. The mixture is quenched with water and the product is extracted with EE. The organic phase is washed with water and brine, dried and concentrated. The crude product is purified by preparative HPLC to give 1.25 g of the product.

$C_{15}H_{12}ClF_2N_5O$ (M=351.74 g/mol)

ESI-MS: 352 [M+H]$^+$

R$_t$ (HPLC): 0.54 min (Method L)

The following compounds are prepared according to the general procedure (Example III.1) described above:

| Ex. | Starting material | Starting material | Structure | Reaction conditions | ESI-MS | HPLC retention time (method) [min] |
|---|---|---|---|---|---|---|
| III.2 | 1.0 eq 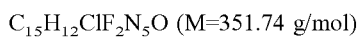 | 1.0 eq | 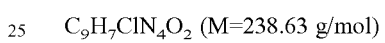 Cl | o/n RT | 215 [M + H]+ | 0.56 (Method J) |

Example IV methyl 1-(6-chloropyridazin-3-yl)-1H-imidazole-4-carboxylate

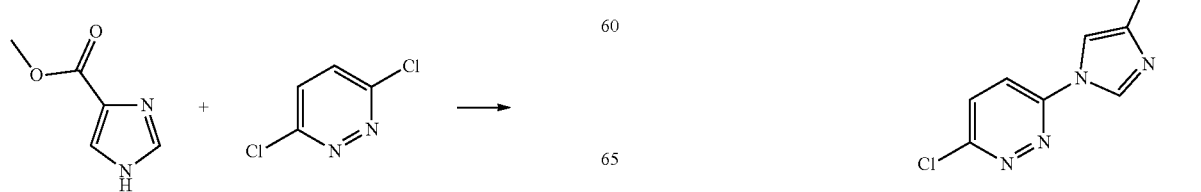

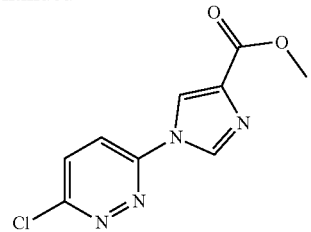

To sodium hydride (1.74 g, 43.6 mmol) in 50 mL DMF is added methyl 1H-imidazole-4-carboxylate (5.0 g, 39.6 mmol) at 0° C. The reaction mixture is stirred for 30 min. To the reaction mixture is added a solution of 3,6-dichloropyridazine (5.9 g, 39.6 mmol) in 30 mL DMF at 0° C. and the mixture is stirred for 20 h to reach RT. The reaction mixture is quenched with water under ice cooling and the precipitation is filtered, washed and dried to give 3.9 g of the product.

$C_9H_7ClN_4O_2$ (M=238.63 g/mol)

ESI-MS: 239 [M+H]$^+$ $^1$H NMR (400 MHz, DMSO-d$_6$) δ=8.74 (d, J=1.3 Hz, 1H), 8.72 (d, J=1.0 Hz, 1H), 8.43 (d, J=9.3 Hz, 1H), 8.25 (d, J=9.3 Hz, 1H), 3.82 (s, 3H)

Example V 1-(6-chloropyridazin-3-yl)-1H-imidazole-4-carboxylic acid

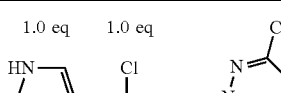

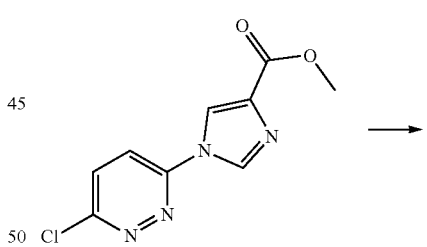

To Example IV (3.79 g, 15.8 mmol) in 100 mL 1,4-dioxane is added 1 M NaOH (16 mL, 16.0 mmol) and is stirred for 18 h at RT. The reaction mixture is quenched with ice and 1 M HCl (16 mL, 16.0 mmol). The precipitation is filtered, washed and dried to yield 3.3 g of the product.

$C_8H_5ClN_4O_2$ (M=224.60 g/mol)

ESI-MS: 225 [M+H]$^+$ $R_t$ (HPLC): 0.58 min (Method A)

Example VI.1

1-(6-chloropyridazin-3-yl)-N-methyl-1H-imidazole-4-carboxamide

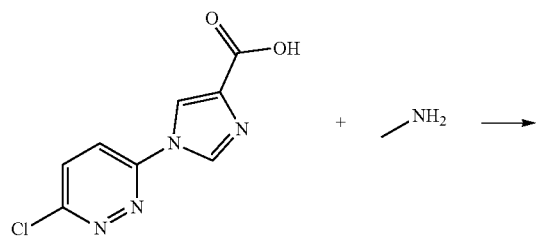

To Example V (1.0 g, 4.45 mmol) in 5 mL DMF are added DIPEA (2.30 mL, 13.4 mmol) and TBTU (1.43 g, 4.45 mmol) and is stirred for 10 min at RT. Methylamine (2.23 mL, 4.45 mmol) is added and the reaction mixture is stirred for 1 h at RT. The mixture is quenched with ice and the precipitation is filtered, washed and dried to afford 0.8 g of the product.

$C_9H_8ClN_5O$ (M=237.65 g/mol)

ESI-MS: 238 [M+H]$^+$ $R_t$ (HPLC): 0.65 min (Method A)

The following compounds are prepared according to the general procedure (Example VI.1) described above:

| Ex. | Starting material | Starting material Structure | Reaction conditions | ESI-MS | HPLC retention time (method) [min] |
|---|---|---|---|---|---|
| VI.2 | V | (structure shown) | 1 h RT | 252 [M+H]+ | 0.66 (Method A) |

Example VII.1

1-(6-chloropyridazin-3-yl)-1H-imidazole-4-carbaldehyde

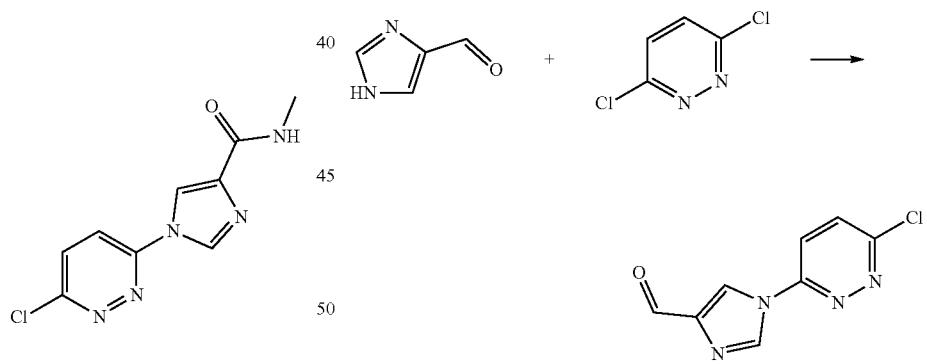

To 1H-imidazole-4-carbaldehyde (4.87 g, 50.7 mmol) in 25 mL DMF are added 3,6-dichloropyridazine (7.55 g, 50.68 mmol) and sodium carbonate (14.0 g, 101.4 mmol) and the reaction mixture is stirred at 80° C. for 18 h. The mixture is quenched with water and the precipitation is filtered, washed and dried to give 5.1 g of the product.

$C_8H_5ClN_4O$ (M=208.60 g/mol)

ESI-MS: 209 [M+H]$^+$ $R_t$ (HPLC): 0.61 min (Method A)

The following compounds are prepared according to the general procedure (Example VII.1) described above:

| Ex. | Starting material | Starting material | Structure | Reaction conditions | ESI-MS | HPLC retention time (method) [min] or NMR description |
|---|---|---|---|---|---|---|
| VII.2 | Cl (3,6-dichloropyridazine) | 2 eq. (imidazole-carbaldehyde) | (bis-imidazolyl pyridazine dialdehyde) | 48 h 50° C. | 269 [M + H]+ | ¹H NMR (400 MHz, DMSO-d₆) δ = 10.03-9.78 (m, 1H), 9.00-8.93 (m, 1H), 8.92-8.84 (m, 1H), 8.69-8.59 (m, 1H) |
| VII.3 | Cl (3,6-dichloropyridazine) | 2 eq. (acetyl imidazole) | (bis-acetylimidazolyl pyridazine) | o/n 100° C. | 297 [M + H]+ | 0.29 (Method J) |
| VII.4 | Cl (3,6-dichloropyridazine) | (3-trifluoromethyl pyrazole) | (6-chloro-3-(3-trifluoromethylpyrazol-1-yl)pyridazine) | o/n 80° C. | 249 [M + H]+ | 0.85 (Method I) |
| VII.5 | Cl (3,6-dichloropyridazine) | (4-trifluoromethyl pyrazole) | (6-chloro-3-(4-trifluoromethylpyrazol-1-yl)pyridazine) | o/n RT | 249 [M + H]+ | 0.86 (Method J) |

Example VIII.1

1-(6-chloropyridazin-3-yl)-1H-imidazole-4-carbonitrile

Example IX.1

3,6-bis(1H-1,2,4-triazol-1-yl)pyridazine

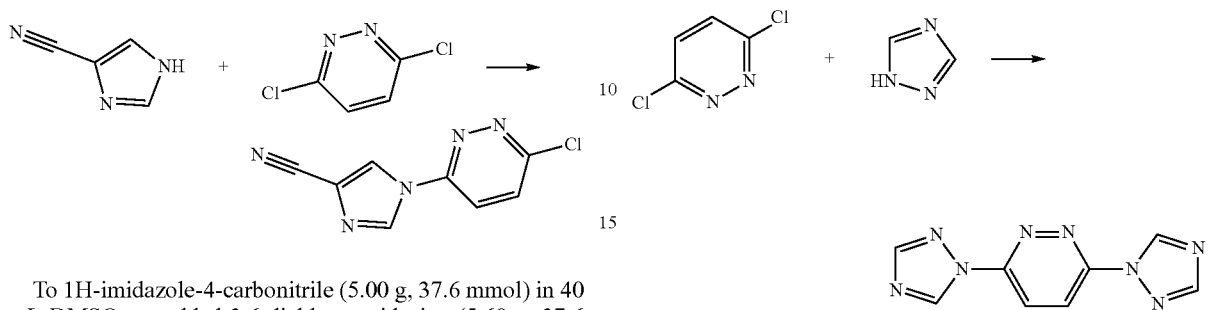

To 1H-imidazole-4-carbonitrile (5.00 g, 37.6 mmol) in 40 mL DMSO are added 3,6-dichloropyridazine (5.60 g, 37.6 mmol) and sodium carbonate (7.79 g, 56.4 mmol) and the reaction mixture is stirred at RT for 18 h. The mixture is quenched with water and the precipitation is filtered. The residue is diluted in EE and extracted with water. The organic phase is dried over MgSO$_4$, filtered and the solvent is removed. Purification by silica column to give 2.1 g of the product.

$C_8H_4ClN_5$ (M=205.60 g/mol)
ESI-MS: 206 [M+H]$^+$
R$_t$ (HPLC): 0.66 min (Method L)

The following compounds are prepared according to the general procedure (Example VIII.1) described above:

To 3,6-dichloropyridazine (500 mg, 3.36 mmol) in 5 mL DMF are added 1H-1,2,4-triazole (460 mg, 6.71 mmol) and cesium carbonate (2.41 g, 7.38 mmol) and the reaction mixture is stirred at 60° C. for 18 h. The mixture is quenched with water and the precipitation is filtered, washed and dried to give 0.7 g of the product.

$C_8H_6N_8$ (M=214.19 g/mol)
ESI-MS: 215 [M+H]$^+$
$^1$H NMR (400 MHz, DMSO-d$_6$) δ=9.66 (s, 1H), 8.47 (s, 1H), 8.44 (s, 1H)

| Ex. | Starting material | Starting material | Structure | Reaction conditions | ESI-MS | HPLC retention time (method) [min] |
|---|---|---|---|---|---|---|
| VIII.2 | 3,6-dichloropyridazine | methylthio-imidazole | 6-chloropyridazinyl-(methylthio)imidazole | o/n RT | 227 [M + H]+ | 0.48 (Method J) |
| VIII.3 | 3,6-dichloropyridazine | pyrazole-carbonitrile | 6-chloropyridazinyl-pyrazole-carbonitrile | o/n RT | 206 [M + H]+ | 0.43 (Method L) |

The following compounds are prepared according to the general procedure (Example IX.1) described above:

| Ex. | Starting material | Starting material | Structure | Reaction conditions | ESI-MS | HPLC retention time (method) [min] or NMR description |
|---|---|---|---|---|---|---|
| IX.2 | 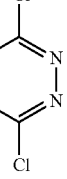 | 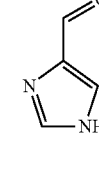 | 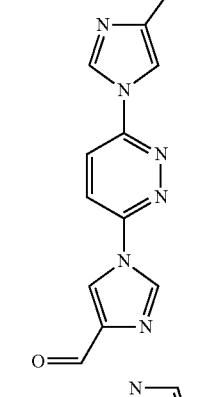 | 48 h 50° C. | 269 [M + H]+ | $^1$H NMR (400 MHz, DMSO-d$_6$) δ = 10.03-9.78 (m, 1H), 9.00-8.93 (m, 1H), 8.92-8.84 (m, 1H), 8.69-8.59 (m, 1H) |
| IX.3 | 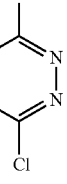 |  | 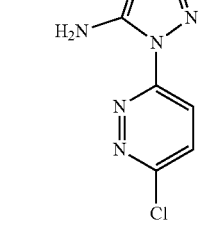 | 18 h RT | | This intermediate is used in the next step without further purification |
| IX.4 | 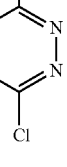 | 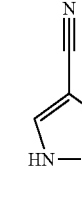 | 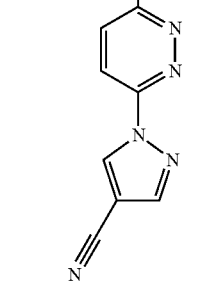 | 18 h RT | 250 [M + H]+ | 0.82 (Method A) |

-continued
| Ex. | Starting material | Starting material | Structure | Reaction conditions | ESI-MS | HPLC retention time (method) [min] or NMR description |
|---|---|---|---|---|---|---|
| IX.5 | 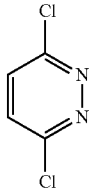 | 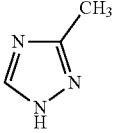 | 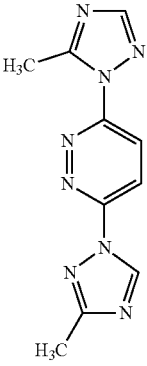 [SMILES: Cc1ncn(-c2ccc(-n3ncnc3C)nn2)n1] | 18 h RT | [M + H]+ | Mixture of 2 regioisomers and is used without any further purification in the next step 0.31 70% + 0.33 30% (Method L) |
| IX.6 | 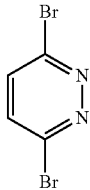 | 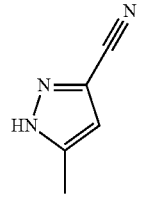 | 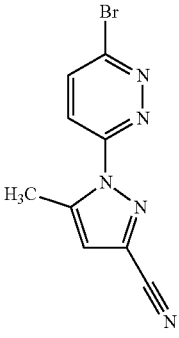 | 18 h RT | 264 [M + H]+ | 0.93 (method A) |

Example X.1

1-[6-(4-cyano-1H-imidazol-1-yl)pyridazin-3-yl]-1H-imidazole-4-carbonitrile

Example XII 3-chloro-6-(4-methanesulfonyl-1H-imidazol-1-yl)pyridazine

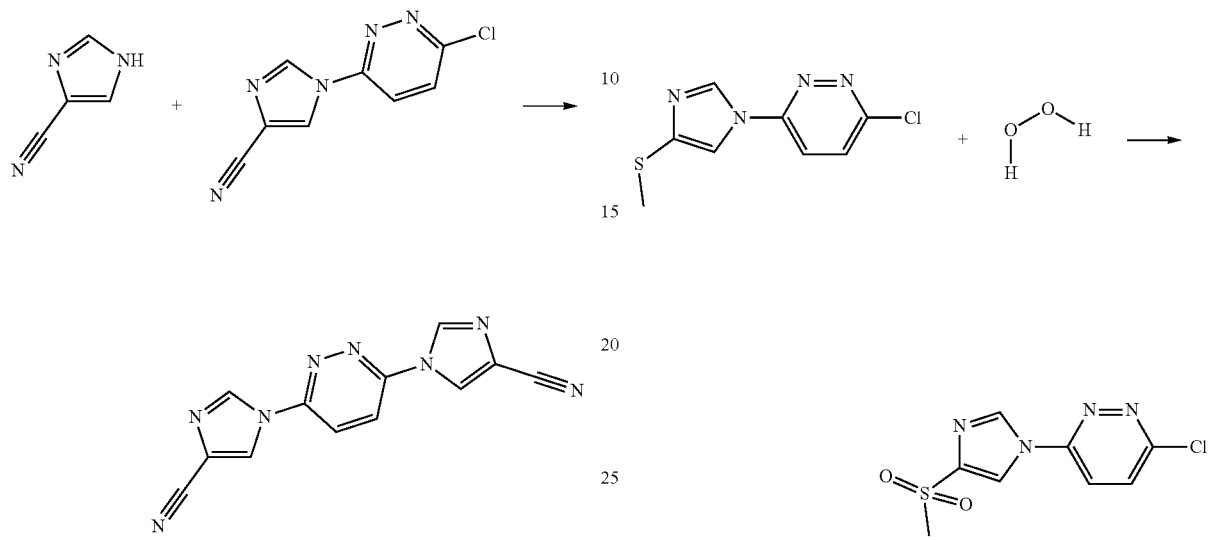

To 1H-imidazole-4-carbonitrile (9.29 g, 99.9 mmol) in 100 mL DMF are added Example VIII.1 (20.5 g, 99.9 mmol) and sodium carbonate (41.4 g, 299 mmol) and the reaction mixture is stirred at 50° C. for 18 h. Addition of 1H-imidazole-4-carbonitrile (5.00 g, 53.7 mmol) and the mixture is stirred at 50° C. for 3 days. The mixture is quenched with water and the precipitate is filtered to give after drying 25.8 g of the product.

$C_{12}H_6N_8$ (M=262.23 g/mol)
ESI-MS: 263 [M+H]$^+$
$R_t$ (HPLC): 0.74 min (Method A)

The following compounds are prepared according to the general procedure (Example X.1) described above:

To Example VIII.2 (100 mg, 0.44 mmol) in 2 mL acetic acid is added aq. $H_2O_2$ (35%) (379 µL, 4.41 mmol) and the mixture is stirred at RT o/n. The reaction mixture is quenched with water and extracted with DCM. The organic phase is washed with brine, dried and concentrated to yield 87 mg of the product.

$C_8H_7ClN_4O_2S$ (M=258.69 g/mol)
ESI-MS: 259 [M+H]$^+$
$R_t$ (HPLC): 0.39 min (Method J)

| Ex. | Starting material | Starting material | Structure | Reaction conditions | ESI-MS | HPLC retention time (method) [min] or NMR description |
|---|---|---|---|---|---|---|
| X.2 | | | 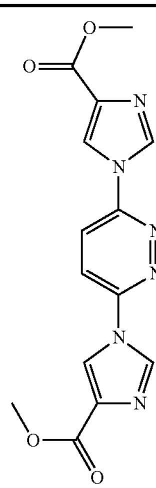 | 18 h 50° C. | 329 [M + H]+ | $^1$H NMR (400 MHz, DMSO-d$_6$) δ = 8.81-8.78 (m, 1H), 8.78-8.75 (m, 1H), 8.63-8.60 (broad s, 1H) |

Example XIII 3-chloro-6-(pyrimidin-5-yl)pyridazine

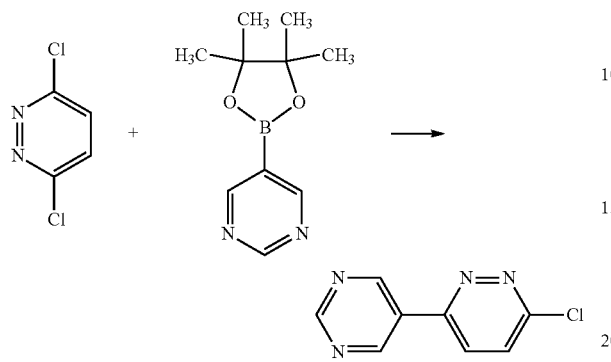

To 3,6-dichloropyridazine (2.23 g, 15.0 mmol) in 25 mL 1,4-dioxane are added under argon 5-(4,4,5,5-tetramethyl-1,3,2-dioxaborolan-2-yl)pyrimidine (3.29 g, 16.0 mmol), Pd(PPh$_3$)$_4$ (346 mg, 0.30 mmol) and 2M aq. Na$_2$CO$_3$ solution (7.5 mL, 15.0 mmol) and the mixture is stirred at 80° C. for 2 h. The reaction mixture is quenched with water and extracted with EE. The organic phase is washed with brine, dried and concentrated. Purification by silica column to yield to 442 mg of the product.

C$_8$H$_5$ClN$_4$ (M=192.60 g/mol)

ESI-MS: 193 [M+H]$^+$ $^1$H NMR (400 MHz, DMSO-d$_6$) Shift=9.51 (s, 2H), 9.36 (s, 1H), 8.52 (d, J=9.0 Hz, 1H), 8.17 (d, J=9.0 Hz, 1H)

Example XIV 3-chloro-6-(4-methanesulfinyl-1H-imidazol-1-yl)pyridazine

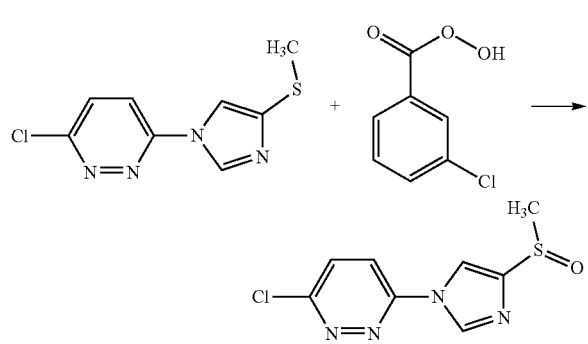

To Example VIII.2 (150 mg, 0.66 mmol) in 1 mL DCM is added 3-chlorobenzene-1-carboperoxoic acid (163 mg, 0.66 mmol) and the mixture is stirred at RT o/n. The reaction mixture is concentrated and used without further purification C$_8$H$_7$ClN$_4$OS (M=242.69 g/mol)

R$_t$ (HPLC): 0.34 min (Method J)

Example XV 2H,4H,5H,6H,7H-pyrazolo[4,3-c]pyridin-4-one

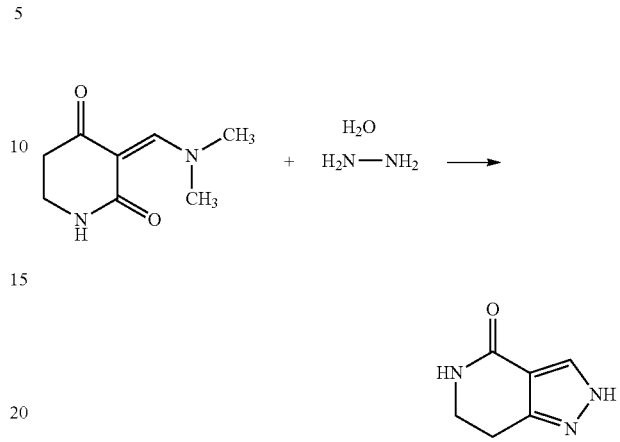

To (3Z)-3-[(dimethylamino)methylidene]piperidine-2,4-dione (1.49 g, 8.84 mmol) in 5 mL of ethanol is added hydrazine hydrate (0.64 mL, 13.3 mmol) and the mixture is stirred at reflux o/n. The reaction mixture is concentrated and purified by silica gel column to give 250 mg of the product.

C$_6$H$_7$N$_3$O (M=137.14 g/mol)

ESI-MS: 138 [M+H]$^+$ $^1$H NMR (400 MHz, DMSO-d$_6$) δ=8.25 (br s, 1H), 8.01 (s, 1H), 7.96 (s, 1H), 3.41 (t, J=6.8 Hz, 2H), 2.83 (t, J=6.8 Hz, 2H)

Example XVI 2-(6-chloropyridazin-3-yl)-2H,4H,5H,6H,7H-pyrazolo[4,3-c]pyridin-4-one

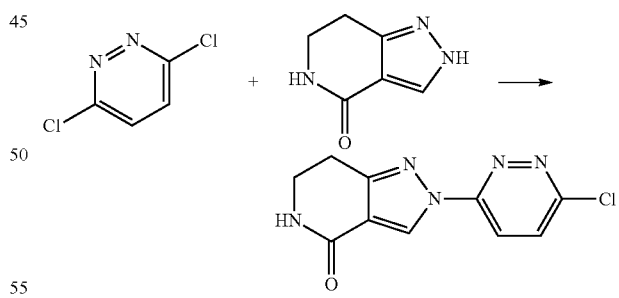

To 3,6-dichloropyridazine (50 mg, 0.33 mmol) in 1 mL of THF are added Example XV (103 mg, 0.75 mmol), sodium tert-butoxide (80 mg, 0.84 mmol) and Pd-PEPPSI (28 mg, 0.03 mmol) and the reaction mixture is stirred at 120° C. o/n. The reaction mixture is quenched with water and purified by preparative HPLC to give 125 mg of the product.

C$_{10}$H$_8$ClN$_5$O (M=249.66 g/mol)

ESI-MS: 250 [M+H]$^+$

R$_t$ (HPLC): 0.32 min (Method L)

Example XVII

6-(pyrazine-2-yl)pyridazin-3-ol

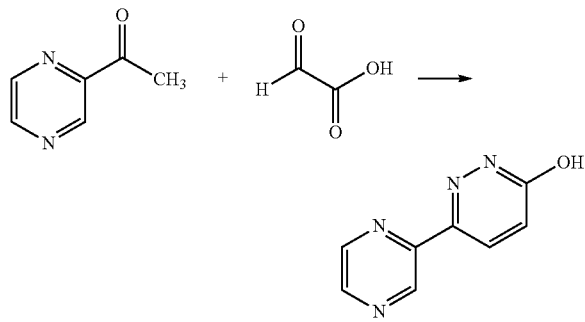

To a mixture of acteylpyrazine (2.0 g, 15.9 mmol) and glyoxylic acid monohydrate (1.54 g, 16.7 mmol) in water (30 mL) triethylamine (2.64 mL, 19.1 mmol) is added within 2 min at 35° C. After 40 min at 40° C., the reaction mixture is cooled to −6° C. and hydrazine hydrate (1.8 mL, 23.8 mmol) is added within 2 min at 5° C. After 1 min acetic acid (2.7 mL, 47.6 mmol) is added and the reaction mixture is heated to 95° C. within 40 min. After 2 h the mixture is slowly cooled to 2° C. The suspension is filtered and washed twice with water. The isolated solid is dried at 50° C. to yield 2.2 g of the product.

MS: 175.110 [M+H]+

$^1$H NMR (400 MHz, DMSO-d$_6$) δ=13.46 (br s, 1H), 9.25 (d, J=1.4 Hz, 1H), 8.74-8.63 (m, 2H), 8.21 (d, J=9.9 Hz, 1H), 7.07 (d, J=9.9 Hz, 1H)

Example XVIII

3-chloro-6-(pyrazine-2-yl)pyridazine

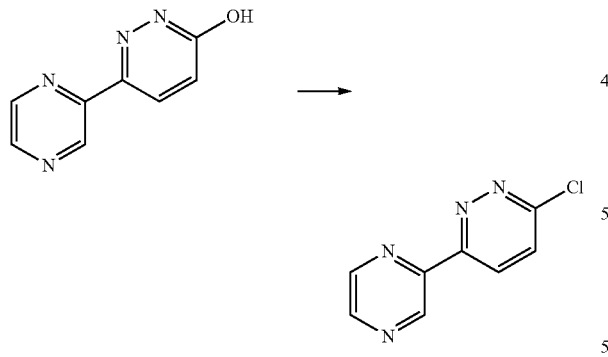

POCl$_3$ (2.3 mL, 25.3 mmol) is added to a heated mixture (70° C.) of 6-(pyrazine-2-yl)pyridazin-3-ol (Example XVII, 4.0 g, 23.0 mmol) in dioxane (36.0 mL) and acetonitrile (4.0 mL). The mixture is stirred at 75° C. for 2.5 h. The hot reaction mixture is added to cooled water (80 mL) while stirring. The reaction flask is rinsed with a mixture of dioxane (5.0 mL) and acetonitrile (5.0 mL) and the suspension is stirred for 2.5 h at 20° C. The suspension is filtered and washed with water. The isolated solid is dried at 50° C. to yield 4.0 g of the product.

MS: 193.080/195.040 [M+H]+

$^1$H NMR (400 MHz, DMSO-d$_6$) δ=9.67 (s, 1H), 8.86 (s, 2H), 8.54 (d, J=9.0 Hz, 1H), 8.13 (d, J=9.0 Hz, 1H)

Preparation of Final Compounds

Example 1

1-[6-({1-[4-(difluoromethyl)phenyl]-4-methyl-1H-1,2,3-triazol-5-yl}methoxy)pyridazin-3-yl]-1H-imidazole-4-carbonitrile

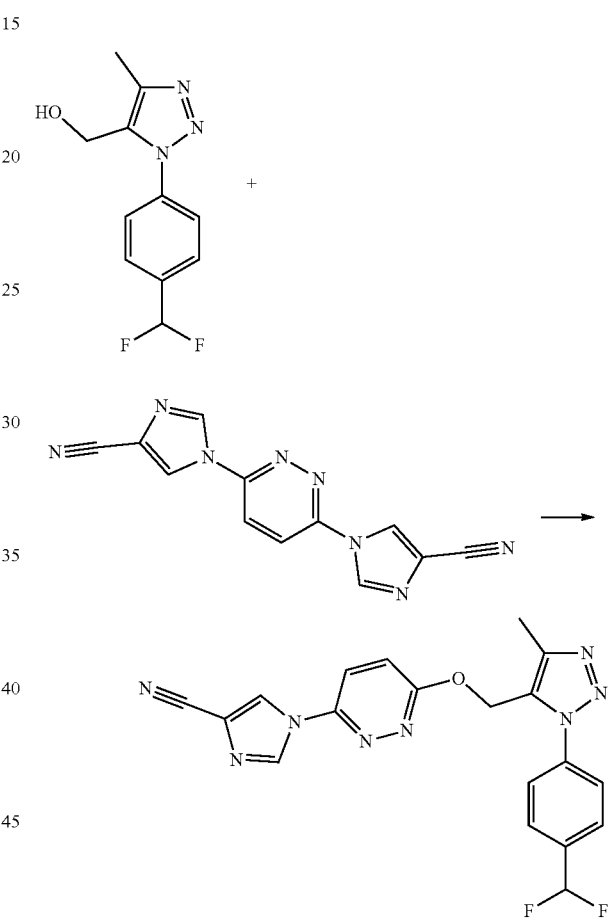

To Example I (20.03 g, 83.74 mmol) in 400 mL ACN are added cesium carbonate (30.01 g, 92.12 mmol) and Example X.1 (21.96 g, 83.74 mmol) and the mixture is stirred for 6 h at 50° C. The mixture is quenched with EE and extracted twice with water. Extraction with 20% aq. KHSO$_4$. The organic phase is washed with brine, dried and concentrated. The precipitation is filtered, washed with EE and dried to yield 26.7 g of the product.

C$_{19}$H$_{14}$F$_2$N$_8$O (M=408.36 g/mol)

ESI-MS: 409 [M+H]$^+$

R$_t$ (HPLC): 0.90 min (Method A)

$^1$H NMR (400 MHz, DMSO-d$_6$) δ=8.91 (d, J=1.3 Hz, 1H), 8.72 (d, J=1.3 Hz, 1H), 8.19 (d, J=9.5 Hz, 1H), 7.80 (s, 4H), 7.57 (d, J=9.4 Hz, 1H), 7.30-6.97 (t, J=55.6 Hz, 1H), 5.67 (s, 2H), 2.44 (s, 3H)

Example 2

4-[6-({1-[4-(difluoromethyl)phenyl]-4-methyl-1H-1,2,3-triazol-5-yl}methoxy)pyridazin-3-yl]pyridin-2-ol

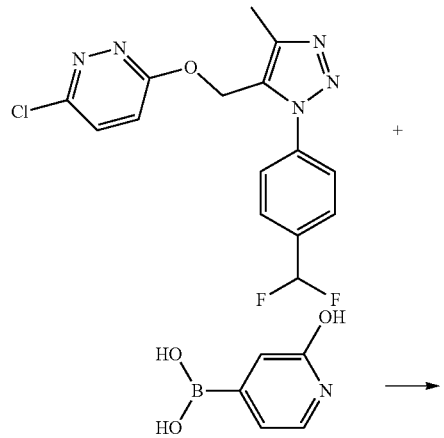

+

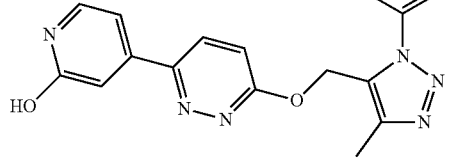

→

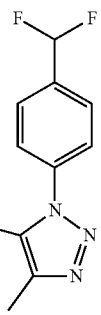

To (2-hydroxypyridin-4-yl)boronic acid (35 mg, 0.150 mmol) is added a solution of Example III.1 (37 mg, 0.100 mmol) in 0.5 mL methanol, 1 mL 1,4 dioxane, 2M aq sodium carbonate solution (0.10 ml, 0.200 mmol) and Pd-PEPPSI (1.68 mg 0.002 mmol) under argon and the reaction mixture is stirred for 2 h at 120° C. The mixture is purified by preparative HPLC to yield 4 mg of the product.

ESI-MS: 411 [M+H]$^+$
$R_t$ (HPLC): 0.60 min (Method B)

The following compounds are prepared according to the general procedure (example 2) described above:

| Ex. | Starting material | Structure | Reaction conditions | ESI-MS | HPLC retention time (method) [min] |
|---|---|---|---|---|---|
| 3 | III.1 | 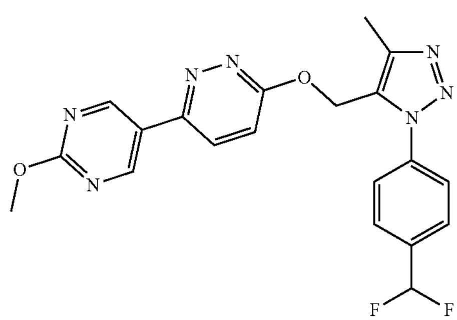 [SMILES: COc1ncc(-c2ccc(OCc3c(C)nnn3-c3ccc(C(F)F)cc3)nn2)cn1] | 2 h 120° C. | 426 [M + H]$^+$ | 0.73 (method B) |
| 4 | III.1 | 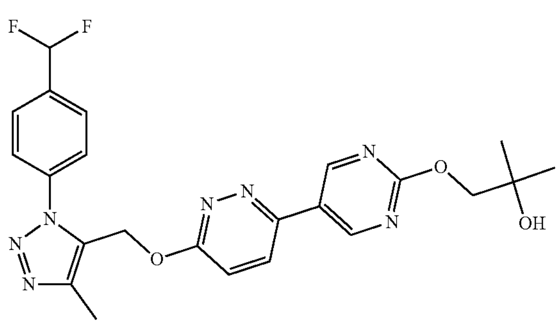 [SMILES: Cc1nnn(-c2ccc(C(F)F)cc2)c1COc1ccc(-c2cnc(OCC(C)(C)O)nc2)nn1] | 2 h 120° C. | 484 [M + H]$^+$ | 0.71 (Method B) |

-continued

| Ex. | Starting material | Structure | Reaction conditions | ESI-MS | HPLC retention time (method) [min] |
|---|---|---|---|---|---|
| 5 | III.1 | 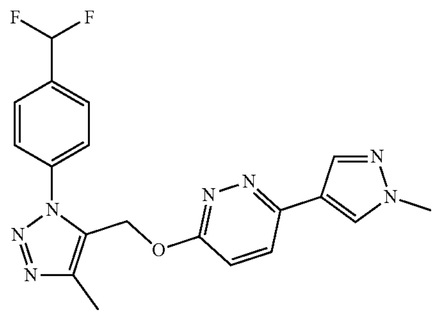 [SMILES: Cc1nnn(-c2ccc(C(F)F)cc2)c1COc1ccc(-c2cnn(C)c2)nn1] | 2 h 120° C. | 398 [M + H]+ | 0.64 (Method B) |
| 6 | III.1 | 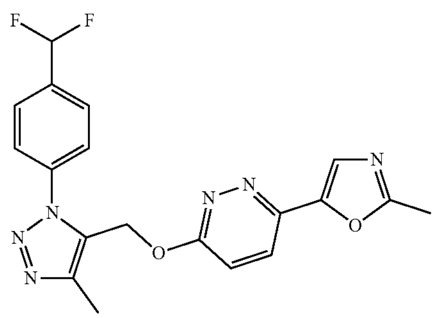 [SMILES: Cc1ncc(-c2ccc(OCc3c(C)nnn3-c3ccc(C(F)F)cc3)nn2)o1] | 2 h 120° C. | 399 [M + H]+ | 0.70 (Method B) |
| 7 | III.1 | 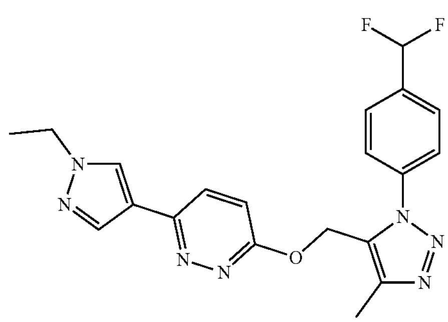 [SMILES: CCn1cc(-c2ccc(OCc3c(C)nnn3-c3ccc(C(F)F)cc3)nn2)cn1] | 2 h 120° C. | 412 [M + H]+ | 0.68 (Method B) |
| 8 | III.1 | 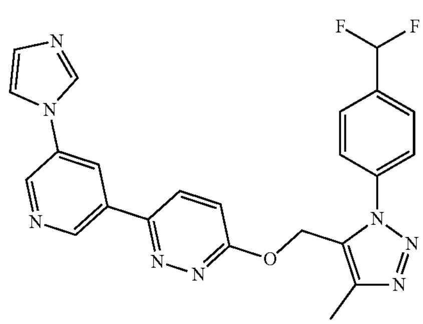 [SMILES: Cc1nnn(-c2ccc(C(F)F)cc2)c1COc1ccc(-c2cncc(-n3ccnc3)c2)nn1] | 2 h 120° C. | 461 [M + H]+ | 0.51 (Method B) |

| Ex. | Starting material | Structure | Reaction conditions | ESI-MS | HPLC retention time (method) [min] |
|---|---|---|---|---|---|
| 9 | III.1 | 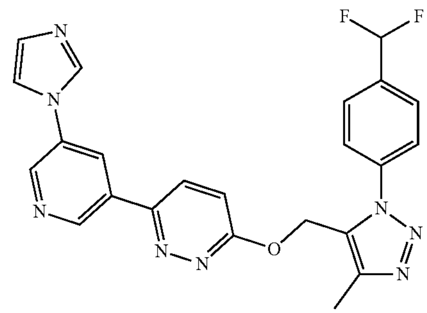 | 2 h 120° C. | 424 [M + H]⁺ | 0.71 (Method B) |
| 10 | III.1 | 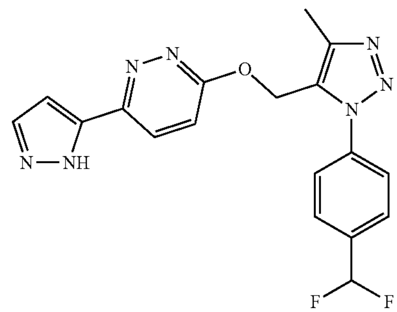 [SMILES: Cc1nnn(-c2ccc(C(F)F)cc2)c1COc1ccc(-c2ccn[nH]2)nn1] | 30 min 120° C. | 384 [M + H]⁺ | 0.62 (Method D) |
| 11 | III.1 | 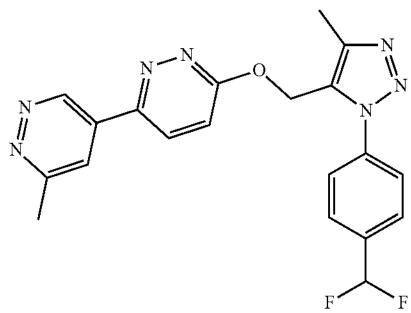 [SMILES: Cc1cc(-c2ccc(OCc3c(C)nnn3-c3ccc(C(F)F)cc3)nn2)cnn1] | 1 h 120° C. | 410 [M + H]⁺ | 0.86 (Method A) |
Example 12
3-({1-[4-(difluoromethyl)phenyl]-4-methyl-1H-1,2,3-triazol-5-yl}methoxy)-6-(3,5-dimethyl-1H-pyrazol-4-yl)pyridazine
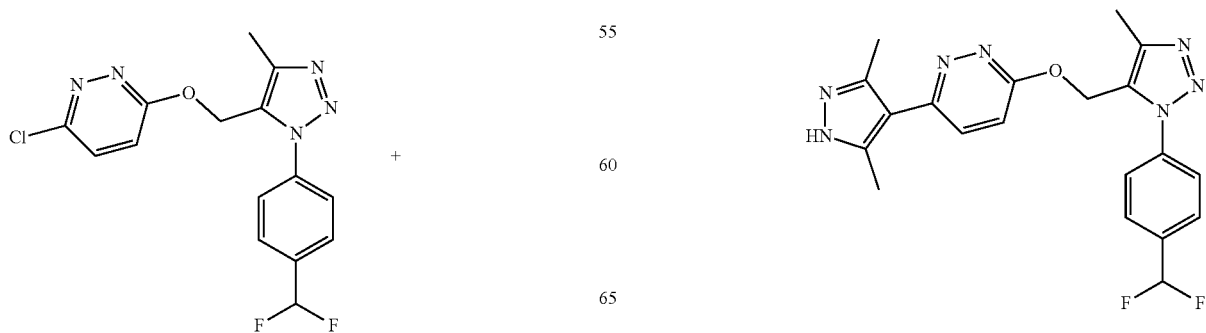

To tert-butyl 3,5-dimethyl-4-(4,4,5,5-tetramethyl-1,3,2-dioxaborolan-2-yl)-1H-pyrazole-1-carboxylate (48 mg, 0.150 mmol) is added a solution of Example III.1 (35 mg, 0.10 mmol) in 0.5 mL methanol, 1 mL 1,4 dioxane, 2 M aq sodium carbonate solution (0.10 mL, 0.20 mmol) and Pd-PEPPSI (0.84 mg 0.001 mmol) under argon and the reaction mixture is stirred for 30 min at 120° C. The reaction mixture is evaporated. The residue is diluted with 2 mL TFA and is stirred for 1 h at RT. The mixture is purified by preparative HPLC to give 29.8 mg of the product.

ESI-MS: 412 [M+H]$^+$

R$_t$ (HPLC): 0.61 min (Method E)

Example 13

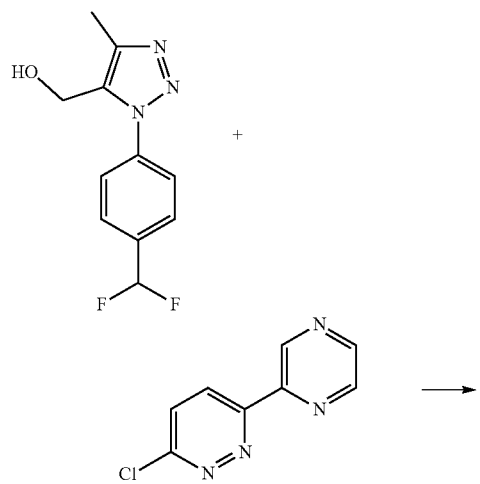

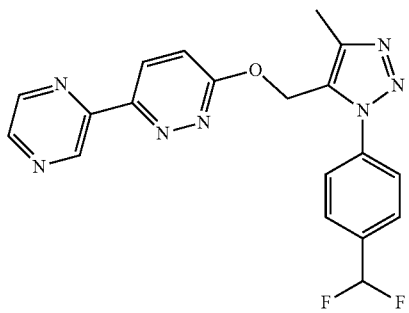

To Example I (500 mg, 2.1 mmol) and Example XVIII (402.6 mg, 2.1 mmol) in 7.5 mL NMP is added dropwise at 0° C. a solution of sodium tert-pentoxide 30% in Me-THF (928 μL, 2.3 mmol) and is stirred for 20 min at RT. 7.5 mL of water is added and is stirred for 30 min at RT. The suspension is filtered and washed twice with 5 mL of water and the residue is dryed at 60° C. to give 717 mg of the product.

ESI-MS: 397 [M+H]$^+$

R$_t$ (HPLC): 0.92 min (method C)

$^1$H NMR (400 MHz, DMSO-d$_6$) δ=9.58 (d, J=1.3 Hz, 1H), 8.78 (m, 2H), 8.40 (d, J=9.3 Hz, 1H), 7.84-7.78 (m, 4H), 7.39 (d, J=9.3 Hz, 1H), 7.32-6.95 (t, J=55.6 Hz, 1H), 5.73 (s, 2H), 2.46 (s, 3H)

The following compounds are prepared according to the general procedure (Example 13) described above:

| Ex. | Starting material | | Structure | 15 min RT Reaction conditions | ESI-MS | HPLC retention time (method) [min] |
|---|---|---|---|---|---|---|
| 14 | I | VI.1 | ![structure] | DCM/DMF 1/1 1.1 eq. NaH 2 h RT | 441 [M + H]$^+$ | 0.84 min (Method A) |
| 15 | I | II.2 | ![structure] | THF 2.0 eq. NaH 18 h RT | 434 [M + H]$^+$ | 0.95 (Method A) |

| Ex. | Starting material | | Structure | 15 min RT Reaction conditions | ESI-MS | HPLC retention time (method) [min] |
|---|---|---|---|---|---|---|
| 16 | I | VI.2 | 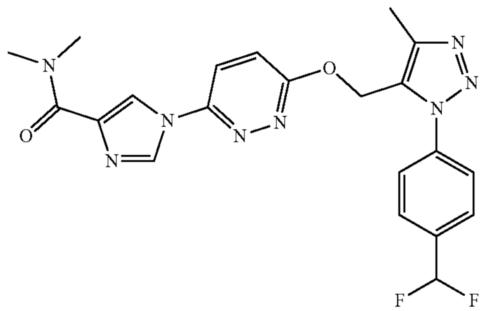 [SMILES: Cc1nnn(-c2ccc(C(F)F)cc2)c1COc1ccc(-n2cnc(C(=O)N(C)C)c2)nn1] | THF 1 h RT | 455 [M + H]⁺ | 0.85 (Method A) |
| 17 | I | VII.2 | 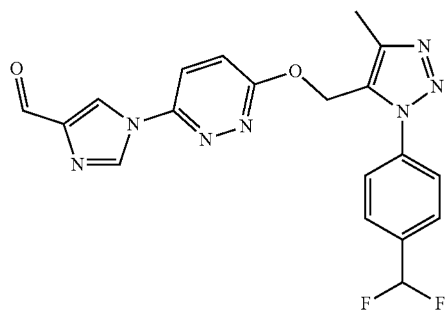 [SMILES: Cc1nnn(-c2ccc(C(F)F)cc2)c1COc1ccc(-n2cnc(C=O)c2)nn1] | THF/DMF 1.5 eq. NaH 18 h 90° C. | 412 [M + H]⁺ | ¹H NMR (400 MHz, DMSO-d$_6$) δ = 9.87 (s, 1H), 8.79 (d, J = 0.8 Hz, 1H), 8.70 (s, 1H), 8.25 (d, J = 9.3 Hz, 1H), 7.81 (S, 4H), 7.55 (d, J = 9.6 Hz, 1H), 7.14 (t, J = 55.6 Hz, 1H), 5.67 (s, 2H), 2.45 (s, 3H) |
| 18 | I | III.2 | 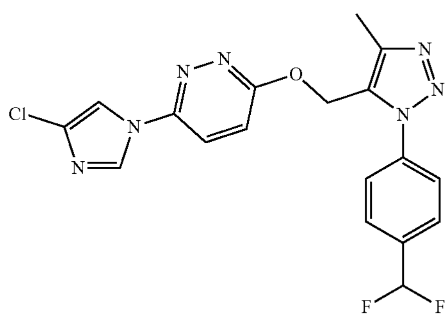 [SMILES: Cc1nnn(-c2ccc(C(F)F)cc2)c1COc1ccc(-n2cnc(Cl)c2)nn1] | THF 1.7 eq. NaH 2 h 0° C. | 418 [M + H]⁺ | ¹H NMR (400 MHz, DMSO-d$_6$) δ = 8.50 (d, J = 1.5 Hz, 1H), 8.14 (d, J = 9.6 Hz, 1H), 8.06 (d, J = 1.8 Hz, 1H), 7.80 (s, 4H), 7.52 (d, J = 9.3 Hz, 1H), 7.14 (t, J = 55.6 Hz, 1H), 5.65 (s, 2H), 2.44 (s, 3H) |
| 19 | I | XII | 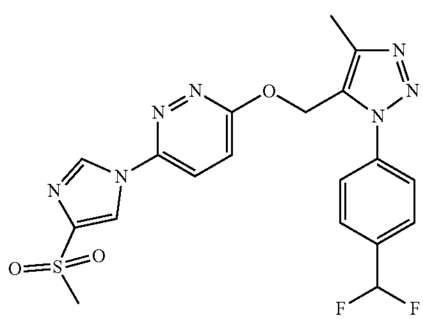 [SMILES: Cc1nnn(-c2ccc(C(F)F)cc2)c1COc1ccc(-n2cnc(S(C)(=O)=O)c2)nn1] | 1.5 eq. NaH o/n RT | 462 [M + H]⁺ | 0.66 (Method F) |
| 20 | I | VIII.3 | 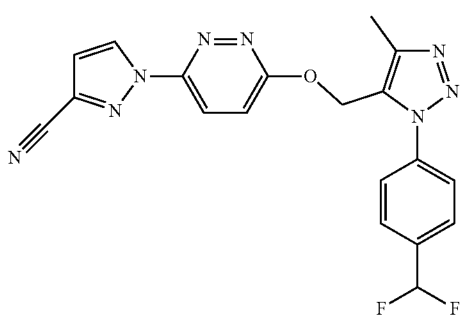 [SMILES: Cc1nnn(-c2ccc(C(F)F)cc2)c1COc1ccc(-n2ccc(C#N)n2)nn1] | THF o/n RT | 409 [M + H]⁺ | 0.87 (Method E) |

-continued

| Ex. | Starting material | | Structure | 15 min RT Reaction conditions | ESI-MS | HPLC retention time (method) [min] |
|---|---|---|---|---|---|---|
| 21 | I | VIII.3 | 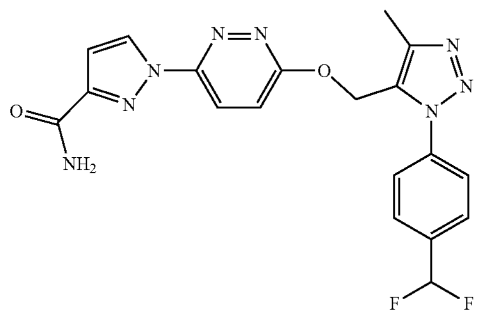 [SMILES: Cc1nnn(-c2ccc(C(F)F)cc2)c1COc1ccc(-n2ccc(C(N)=O)n2)nn1] | THF o/n RT | 427 [M + H]+ | 0.67 (Method B) |
| 22 | I | XIII | 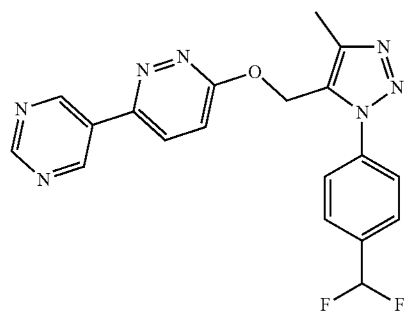 [SMILES: Cc1nnn(-c2ccc(C(F)F)cc2)c1COc1ccc(-c2cncnc2)nn1] | THF 1 h RT | 396 [M + H]+ | 0.62 (Method H) |
| 23 | I | XIV | 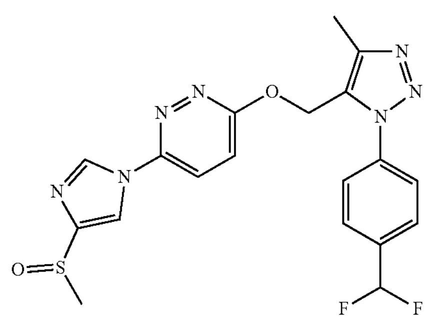 [SMILES: Cc1nnn(-c2ccc(C(F)F)cc2)c1COc1ccc(-n2cnc(S(C)=O)c2)nn1] | o/n RT | 446 [M + H]+ | 0.6 (Method J) |
| 24 | I | VII.4 | 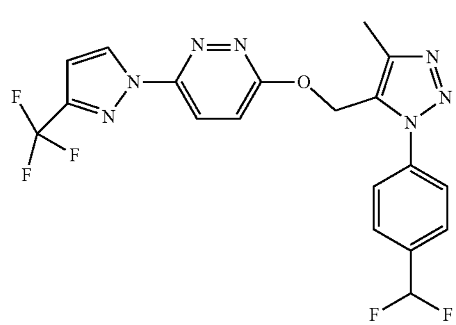 [SMILES: Cc1nnn(-c2ccc(C(F)F)cc2)c1COc1ccc(-n2ccc(C(F)(F)F)n2)nn1] | THF o/n RT | 452 [M + H]+ | 0.94 (Method H) |

| Ex. | Starting material | | Structure | 15 min RT Reaction conditions | ESI-MS | HPLC retention time (method) [min] |
|---|---|---|---|---|---|---|
| 25 | I | VII.5 | 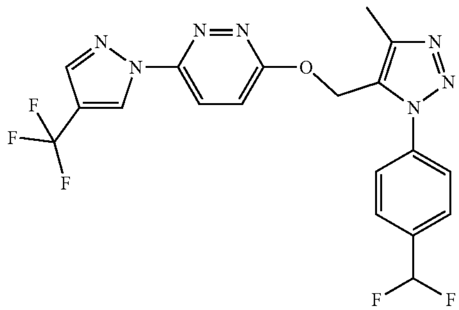 [SMILES: Cc1nnn(-c2ccc(C(F)F)cc2)c1COc1ccc(-n2cc(C(F)(F)F)cn2)nn1] | THF o/n RT | 452 [M + H]⁺ | 0.97 (Method E) |
| 26 | I | XVI | 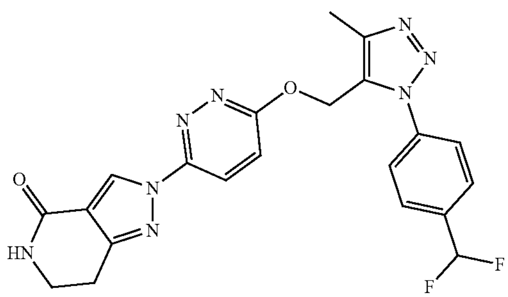 [SMILES: Cc1nnn(-c2ccc(C(F)F)cc2)c1COc1ccc(-n2cc3c(n2)CCNC3=O)nn1] | THF o/n 75° C. | 453 [M + H]⁺ | 0.74 (Method B) |

Example 27

1-[6-({1-[4-(difluoromethyl)phenyl]-4-methyl-1H-1,2,3-triazol-5-yl}methoxy)pyridazin-3-yl]-1H-imidazole-4-carboxamide

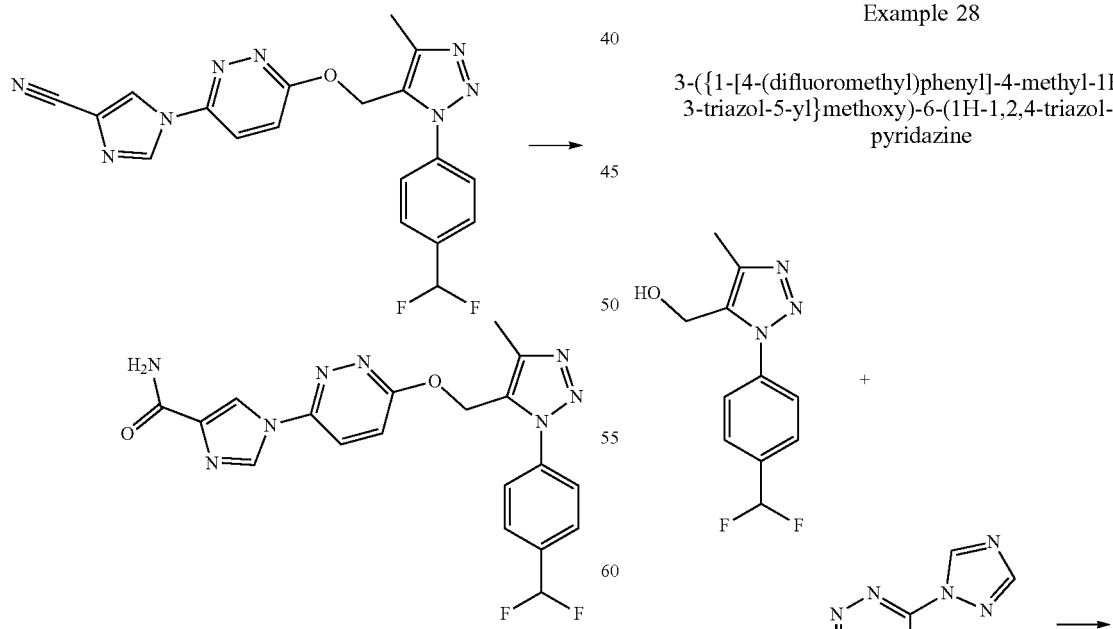

To Example 1 (20 mg, 0.049 mmol) in 1 mL water is added conc. $H_2SO_4$ (2 mL) and is stirred at RT for 18 h. The mixture is quenched with ice water and $NaHCO_3$. The product is extracted with EE. The organic phase is washed with water and brine, dried and concentrated. The crude product is purified by preparative HPLC to give 5 mg of the product.

ESI-MS: 427 [M+H]⁺

$R_t$ (HPLC): 0.82 min (Method A)

Example 28

3-({1-[4-(difluoromethyl)phenyl]-4-methyl-1H-1,2,3-triazol-5-yl}methoxy)-6-(1H-1,2,4-triazol-1-yl)pyridazine

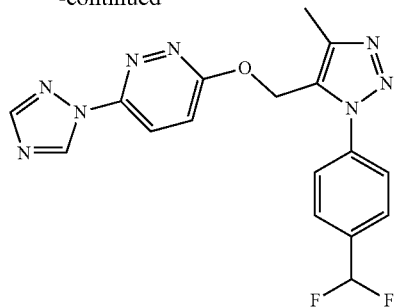

To Example I (50 mg, 0.21 mmol) in 2 mL ACN are added cesium carbonate (204 mg, 0.63 mmol) and Example IX.1 (45 mg, 0.21 mmol) and the mixture is stirred for 18 h at 80° C. The reaction mixture is concentrated and purified by silica gel column to give 45 mg of the product.

ESI-MS: 385 [M+H]$^+$

R$_t$ (HPLC): 0.90 min (Method A)

The following compounds are prepared according to the general procedure (Example 27) described above:

| Ex. | Starting material | | Structure | Reaction conditions | ESI-MS | HPLC retention time (method) [min] |
|---|---|---|---|---|---|---|
| 29 | I | X.2 | 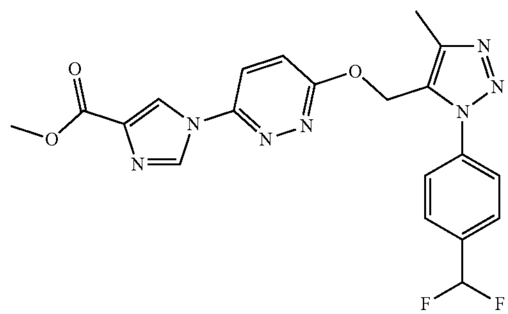 [SMILES: COC(=O)c1cn(-c2ccc(OCc3c(C)nnn3-c3ccc(C(F)F)cc3)nn2)cn1] | DMF 72 h 50° C. | 442 [M + H]$^+$ | 0.90 (method A) |
| 30 | I | IX.3 | 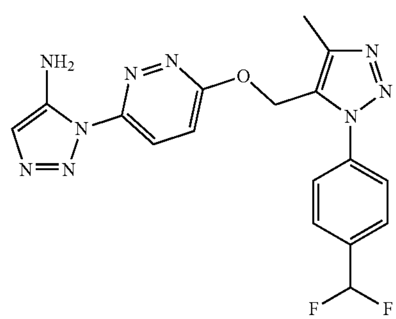 [SMILES: Cc1nnn(-c2ccc(C(F)F)cc2)c1COc1ccc(-n2nncc2N)nn1] | 18 h 60° C. | 400 [M + H]$^+$ | 0.61 (Method D) |
| 31 | I | IX.4 | 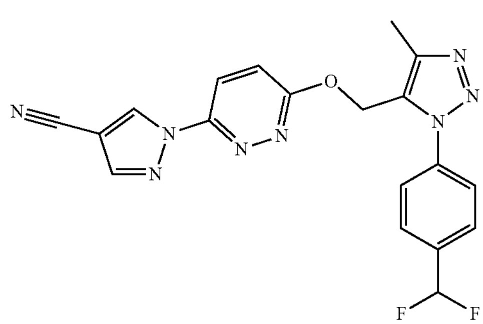 [SMILES: Cc1nnn(-c2ccc(C(F)F)cc2)c1COc1ccc(-n2cc(C#N)cn2)nn1] | 18 h 60° C. | 409 [M + H]$^+$ | 0.82 (Method B) |

-continued

| Ex. | Starting material | | Structure | Reaction conditions | ESI-MS | HPLC retention time (method) [min] |
|---|---|---|---|---|---|---|
| 32 | I | VII.3 | 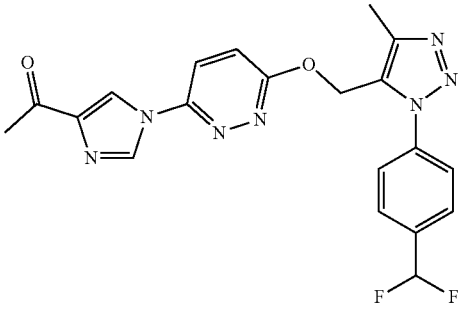 [SMILES: CC(=O)c1cn(-c2ccc(OCc3c(C)nnn3-c3ccc(C(F)F)cc3)nn2)cn1] | DMF o/n 90° C. | 426 [M + H]⁺ | 0.65 (Method F) |
| 33 | I | IX.5 | 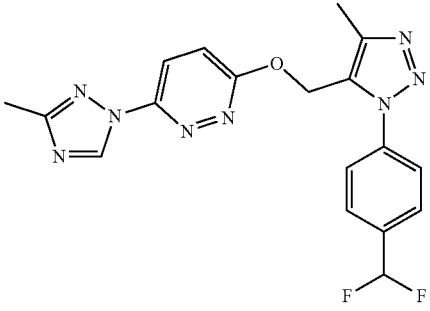 [SMILES: Cc1ncn(-c2ccc(OCc3c(C)nnn3-c3ccc(C(F)F)cc3)nn2)n1] | 18 h 80° C. | 399 [M + H]⁺ | 0.92 (Method A) |
| 34 | I | IX.6 | 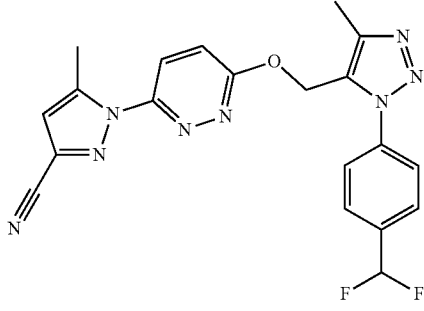 [SMILES: Cc1nnn(-c2ccc(C(F)F)cc2)c1COc1ccc(-n2nc(C#N)cc2C)nn1] | 18 h 60° C. | 423 [M + H]⁺ | 0.82 (Method G) |

Example 35

{1-[6-({1-[4-(difluoromethyl)phenyl]-4-methyl-1H-1,2,3-triazol-5-yl}methoxy)pyridazin-3-yl]-1H-imidazol-4-yl}methanamine

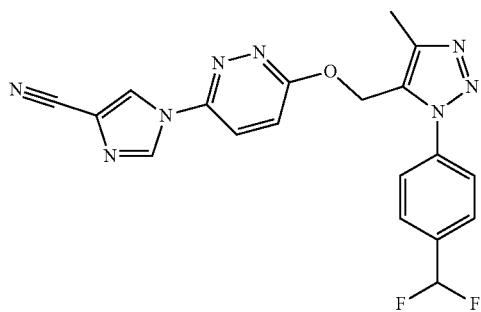

→

-continued

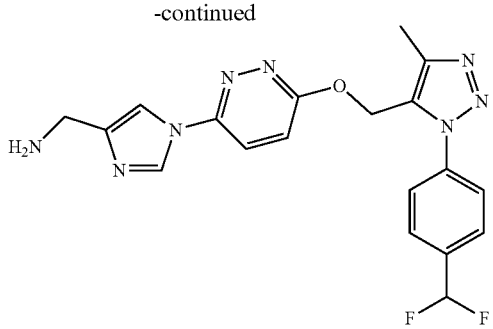

To Example 1 (200 mg, 0.49 mmol) in 10 mL methanolic ammonia solution is added Ra—Ni (50 mg) and stirred at RT and 50 psi under hydrogen atmosphere for 16 h. The reaction mixture is filtered and concentrated by evaporation. The crude product is purified by preparative HPLC to yield to 120 mg of the product.

ESI-MS: 413 [M+H]⁺

$R_t$ (HPLC): 0.54 min (Method D)

Example 36

({1-[6-({1-[4-(difluoromethyl)phenyl]-4-methyl-1H-1,2,3-triazol-5-yl}methoxy)pyridazin-3-yl]-1H-imidazol-4-yl}methyl)trimethylazanium trifluoroacetate

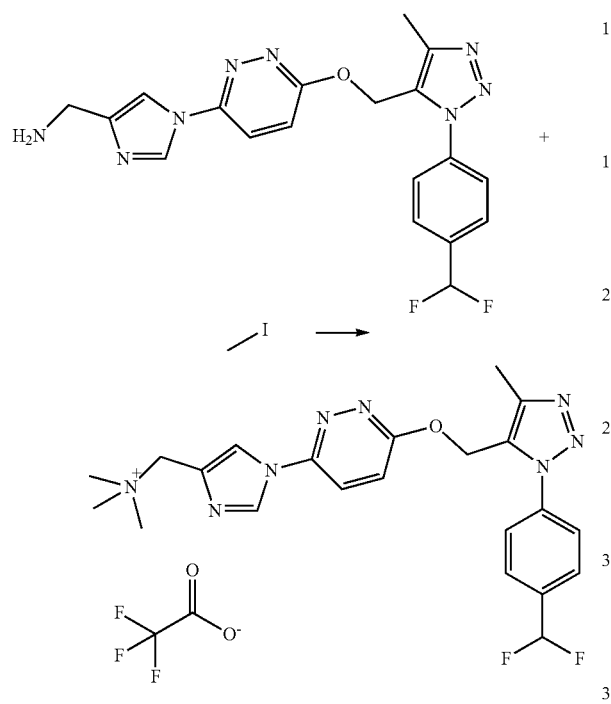

To Example 35 (50 mg, 0.12 mmol) in 1 mL THF are added DIPEA (62 µL, 0.36 mmol) and methyl iodide (15 µl, 0.24 mmol) and stirred at RT for 20 h. The reaction mixture is purified by preparative HPLC to give 35 mg of the product.

ESI-MS: 455 [M]$^+$

R$_t$ (HPLC): 0.74 min (Method A)

Example 37

1-[6-({1-[4-(difluoromethyl)phenyl]-4-methyl-1H-1,2,3-triazol-5-yl}methoxy)pyridazin-3-yl]-1H-imidazole-4-carboxylic acid

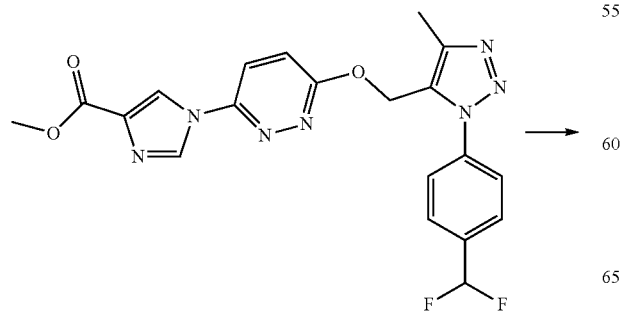

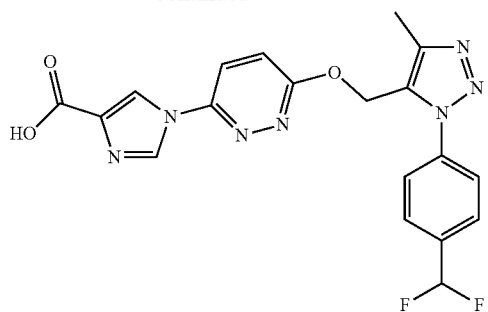

To Example 29 (120 mg, 0.27 mmol) in 6 mL 1,4-dioxane are added 1M NaOH (272 µl, 0.54 mmol) and 1 mL methanol and stirred at RT for 4 h. Addition of 1 M NaOH (272 µL, 0.54 mmol) and the mixture is stirred at RT for 18 h. The reaction mixture is neutralized with 1 M HCl and concentrated. The residue is diluted in DCM/MeOH 9:1, filtered, concentrated and dry to give 118 mg of the product.

ESI-MS: 428 [M+H]$^+$

R$_t$ (HPLC): 0.82 min (Method A)

Example 38

{1-[6-({1-[4-(difluoromethyl)phenyl]-4-methyl-1H-1,2,3-triazol-5-yl}methoxy)pyridazin-3-yl]-1H-imidazol-4-yl}methanol

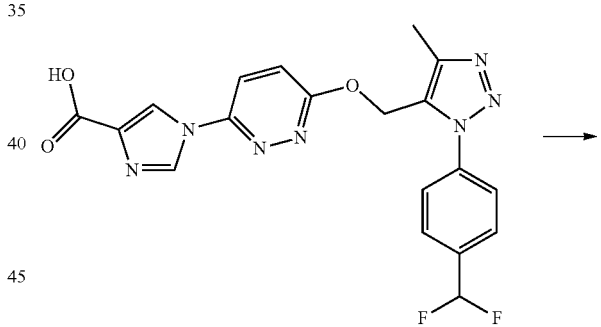

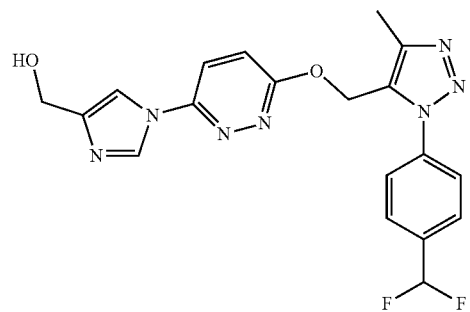

To Example 37 (110 mg, 0.26 mmol) in 4 mL THF is added 1,1'-carbonyldiimidazol (100 mg, 0.62 mmol) and the mixture is stirred at RT for 1 h. This solution is added dropwise to a solution of sodium borohydride (100 mg, 2.64 mmol) in 2 mL water and stirred at RT for 1 h. The reaction mixture is acidified to ph 2 with aq. KHSO$_4$ solution (20%) and extracted with EE. The organic phase is dried, filtered and the solvent is removed. Purification by preparative HPLC is performed and yield to 30 mg of the product.

ESI-MS: 414 [M+H]$^+$

R$_t$ (HPLC): 0.73 min (Method A)

Example 39 (General Route)

2-{1-[6-({1-[4-(difluoromethyl)phenyl]-4-methyl-1H-1,2,3-triazol-5-yl}methoxy)pyridazin-3-yl]-1H-imidazol-4-yl}propan-2-ol

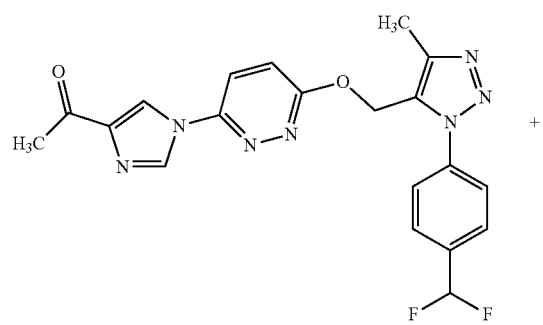

+

-continued

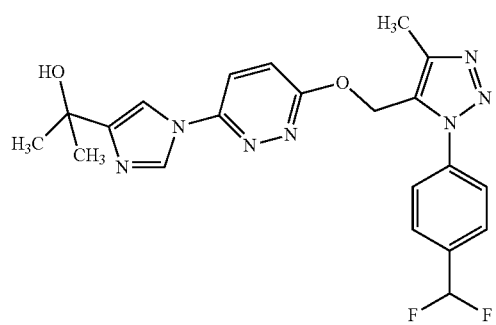

To Example 32 (86 mg, 0.20 mmol) in 3 mL THF is added under ice cooling methylmagnesium bromide (433 μl, 0.61 mmol) and the mixture is stirred at 00° C. for 1 h. Addition under ice cooling of bromo(methyl)magnesium (150 μl, 0.21 mmol) and the mixture is stirred at RT for 18 h. Addition under ice cooling of bromo(methyl)magnesium (200 μL, 0.28 mmol) and the mixture is stirred at RT for 2 h. The reaction mixture is quenched with cold NH$_4$Cl solution (20%) and extracted with EE. The organic phase is dried, filtered and the solvent is removed. Purification by preparative HPLC is performed to give 45 mg of the product.

ESI-MS: 442 [M+H]$^+$

R$_t$ (HPLC): 0.75 min (Method A)

The following compounds are prepared according to the general procedure (Example 39) described above:

| Ex. | Starting material | Structure | Reaction conditions | ESI-MS | HPLC retention time (method) [min] |
|---|---|---|---|---|---|
| 40 | 39 Me—MgBr | 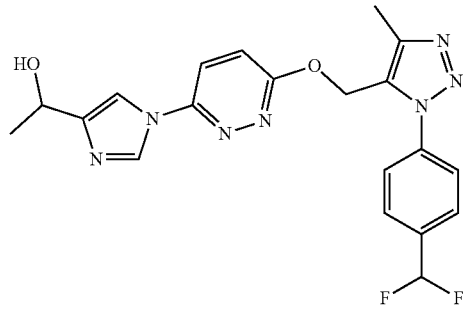 | 18 h RT | 428 [M + H]$^+$ | 0.75 (method A) |

Biological Examples

Assay A: In Vitro Inhibition of $^3$H-Flumazenil ($^3$H-Ro 15-1788) Binding HEK Cells Expressing the Human GABA$_A$ $\alpha_5\beta_3\gamma_{2s}$ Receptor The benzodiazepine modulator unit can selectively be labelled with the antagonist $^3$H-flumazenil.

The affinity of $^3$H-flumazenil for different subunit combinations have been reported to be 1.0 nM, 1.1 nM, 1.5 nM and 0.4 nM for $\alpha_1\beta_2\gamma_2$, $\alpha_2\beta_2\gamma_2$, $\alpha_3\beta_2\gamma_2$ and $\alpha_5\beta_2\gamma_{2s}$ receptors, respectively, and 107 nM and 90 nM for $\alpha_4\beta_2\gamma_2$ and $\alpha_6\beta_2\gamma_2$ receptors (see Sieghart; Pharmacol. Rev. 1995 47 181-234).

The pharmacology of the mutated $\alpha_5\beta_3\gamma_{2s}$ GABA$_A$ receptor is similar to that of the wild type receptor with respect 3H-flumazenil binding.

Cell Cultures and Membrane Preparation

HEK-293 cell lines with stable expression of recombinant human GABA$_A$ $\alpha_5\beta_3\gamma_{2s}$ receptors (plasmid H46/E9/B10) are seeded in T175 polystyrene flasks or roller bottles (1700 cm$^2$, Fisher Scientific CCI-431191), and cultured (37 C, 5% CO~) in Dulbecco's Modified Eagle Medium (DMEM) with GlutaMAX™ supplemented with 10% fetal bovine serum and one or both of the following antibiotics: hygromycin B (50 pg/ml; $\gamma_2$ subunit) or G418 (0.5 mg/ml; 05 subunit).

When the cultures reach confluency, the DMEM is removed and the cells are washed (10 ml for T175 flasks; 50 ml for roller bottles) once in Dulbecco's Phosphate Buffered Saline (DPBS). Following addition of DPBS to the cultures (10 ml for T175 flasks; 100 ml for roller bottles) for approximately 5 min cells are easily detached from the surface by shaking or tapping the flask gently. The cell suspension is transferred to Falcon tubes and centrifuged at 23,500×g for 10 min at 2° C. The pellet is washed once in 15 ml Tris-citrate buffer (50 mM, pH 7.1) using an Ultra-Turrax homogenizer and centrifuged at 2° C. for 10 min at 27,000×g. The washed pellet is re-suspended in 15 ml Tris-citrate buffer and frozen at −80° C. until the day of the binding experiment.

Assay

On the day of the experiment the cell membrane preparation is thawed and centrifuged at 2° C. for 10 min at 27,000×g. The pellet is re-suspended, using an Ultra-Turrax homogenizer in Tris-citrate buffer, to 15-50 pg protein per assay and then used for binding assays.

Aliquots of 500 μl cell suspension are added to 25 μl of test compound solution and 25 μl of $^3$H-flumazenil (1 nM, final concentration), mixed and incubated for 40 min at 2° C. Non-specific binding is determined using clonazepam (1 μM, final concentration).

All dilutions of test compounds and incubation of assay are performed in glass vials/96-vial plates. Solutions of test compounds and $^3$H-flumazenil are prepared 22× the desired final concentration. Compounds are dissolved in 100% DMSO (10 mM stock), diluted in 48% ethanol-water, and tested in triplicate in serial 1:3 or 1:10 dilutions. When screening large numbers of compounds only one concentration of each compound is tested in single wells. Reference compounds are not included routinely, but for each experiment performed total and nonspecific binding is compared to data obtained during validation of the assay.

Binding is either terminated by rapid filtration onto 1) Whatman GF/C glass fibre filters using a Brandel Cell harvester, followed by 5 washes with 1 ml ice-cold buffer or onto 2) UniFilter GF/C glass fibre filter plates using a Tomtec cell harvester, followed by washing with approximately 5 ml ice-cold buffer.

The amount of radioactivity on the filters is determined by conventional liquid scintillation counting using a
1) Tri-Garb™ counter (PerkinElmer Life and Analytical Sciences) for separate large filters or
2) Topcount™ counter (PerkinElmer Life and Analytical Sciences) for 96-well filter plates. Specific binding is total binding minus non-specific binding.

Calculations 25-75% inhibition of specific binding must be obtained before calculation of an IC$_{50}$ (the concentration (μM) of the test compound which inhibits the specific binding of $^3$H-flumazenil by 50%).

The IC$_{50}$ value for a test compound is determined based on the equation:

$$B = 100 - (100 * C^n / (IC_{50}^n + C^n))$$

where B is the binding in percentage of total specific binding; C is the concentration of test compound; and n is the Hill coefficient. For screening purposes n is set to 1. The IC$_{50}$ value is calculated from the concentration response curves by the non-linear regression method using the curve-fitting program GraphPad Prism.

The Ki value for a test compound can be calculated from the IC$_{50}$ value using the equation by Cheng and Prusoff:

$$K = IC_{50}/(1+L/K_d)$$

where the K$_d$ for $^3$H-flumazenil is 0.36 nM, and L is the measured concentration of $^3$H-flumazenil in the inhibition assay.

Assay B: In vitro evaluation of modulation of $\alpha_5\beta_2\gamma_2$ GABA$_A$ receptor.

Modulatory efficacy of compounds of formula (I) is determined electrophysiological recordings in oocytes using the two-electrode voltage clamp (TEVC) technique. Oocytes are injected with cRNA for human GABA$_A$ receptor subunits $\alpha_5$, $\beta_2$ and $\gamma_2$ in a 3:1:3 ratio and modulatory efficacy is evaluated by co-applications with a submaximal EC$_{5-20}$ GABA concentration (0.5 μM) termed GABA control. As a standard, the compounds are tested in five concentrations (3.16, 0.316, 0.0316, 0.00316 and 0.000316 μM) on each oocyte starting with the lowest concentration. Background subtracted peak current amplitudes are normalized to the respective GABA control current, converted to % change and depicted +/−S.E.M. as a function of increasing compound concentrations. Plotted datapoints are fitted to the empirical Hill equation using non-linear regression. 95% confidence intervals for maximal efficacy (Bottom) and potency (Log EC$_{50}$) are derived from this fitting routine.

| Example | Assay A: GABA$_A$ $\alpha_5\beta_3\gamma_{2s}$ Ki [nM] | Assay B: GABA$_A$ $\alpha_5\beta_3\gamma_2$ EC$_{50}$ [nM] | Assay B: GABA$_A$ $\alpha_5\beta_3\gamma_2$ Emax vs GABA [nM] |
|---|---|---|---|
| 1 | 0.126 | 1.5 | −23.3 |
| 2 | 0.086 | 6.0 | −57.0 |
| 3 | 0.160 | 13.5 | −44.3 |
| 4 | 0.870 | 22.8 | −41.5 |
| 5 | 0.110 | 5.8 | −37.7 |
| 6 | 0.110 | 6.9 | −33.3 |
| 7 | 0.032 | 6.0 | −32.0 |
| 8 | 0.055 | 17.0 | −19.5 |
| 9 | 0.250 | 47.5 | −12.0 |
| 10 | 0.120 | 5.8 | −18.0 |
| 11 | 0.058 | 10.3 | −17.6 |
| 12 | 0.900 | 13.0 | −26.0 |

-continued

| Example | Assay A: GABA$_A$ α$_5$β$_3$γ$_{2s}$ Ki [nM] | Assay B: GABA$_A$ α$_5$β$_3$γ$_2$ EC$_{50}$ [nM] | Assay B: GABA$_A$ α$_5$β$_3$γ$_2$ Emax vs GABA [nM] |
|---|---|---|---|
| 13 | 0.249 | 9.0 | −23.0 |
| 14 | 0.071 | 2.3 | −47.3 |
| 15 | 0.110 | 1.4 | −42.5 |
| 16 | 0.160 | — | 0.0 |
| 17 | 0.089 | 1.7 | −23.0 |
| 18 | 0.056 | 3.7 | −27.5 |
| 19 | 0.380 | 7.7 | −25.0 |
| 20 | 0.009 | 4.4 | −19.7 |
| 21 | 0.047 | — | 2.0 |
| 22 | 0.110 | 0.5 | −17.3 |
| 23 | 0.270 | 2.0 | −12.0 |
| 24 | 0.250 | 76.9 | −9.0 |
| 25 | 0.350 | — | −0.7 |
| 26 | 0.120 | 3.4 | −27.0 |
| 27 | 0.036 | 0.4 | −35.2 |
| 28 | 0.546 | 5.5 | −25.0 |
| 29 | 0.063 | 1.8 | −29.0 |
| 30 | 0.070 | 2.4 | −24.7 |
| 31 | 0.210 | 7.4 | −23.0 |
| 32 | 0.039 | 5.7 | −22.8 |
| 33 | 0.163 | 11.2 | −22.0 |
| 34 | 0.035 | — | −4.3 |
| 35 | 0.057 | 2.1 | −21.7 |
| 36 | 0.120 | 6.2 | −31.5 |
| 37 | 0.810 | 4.7 | −28.2 |
| 38 | 0.200 | 1.7 | −23.0 |
| 39 | 0.140 | 1.8 | −17.3 |
| 40 | 0.160 | 1.9 | −17.0 |

These data show that the compounds of the present invention show target engagement and a strong negative modulation of the GABA receptor function. The data also show that the compounds have improved properties with respect to GABA$_A$5R binding, which translates in lower efficacious doses of the compounds for disease treatment (see also: Ballard, T. M., et al. (2009). RO4938581, a novel cognitive enhancer acting at GABA$_A$ α5 subunit-containing receptors. Psychopharmacology (2009) 202: 207-223; J. Pharmacol. Exp. Ther. (2006) 316: 1335-1345.)

Assessment of Efflux in Madin-Darby Canine Kidney (MDCK) Cells Transfected with the 30 Human MDR1 Gene to Assess Brain Penetration (Drug Metabolism and Disposition February 2008, 36 (2) 268-275; DOI: https://doi.org/10.1124/dmd.107.017434) Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the 35 brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable.

MDCK-MDR1 cells (1-2×10e5 cells/1 cm2 area) are seeded on filter inserts (Costar transwell polycarbonate or PET filters, 0.4 μm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$×7H$_2$O, 0.41 mM NaH$_2$PO$_4$×H$_2$O, 15 mM HEPES, 20 mM glucose, 0.25% BSA, pH 7.4) to prepare the transport solutions (0.1-300 μM compound, final DMSO <=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

| Example | MDCK-PGP A-B [10−6 cm/s] | MDCK-PGP Efflux ratio [PEBA/PEAB] |
|---|---|---|
| 1 | 18.1 | 2.6 |
| 3 | 59.7 | 0.6 |
| 6 | 67.8 | 0.7 |
| 7 | 17.7 | 2.7 |
| 9 | 42.4 | 0.8 |
| 10 | 22.4 | 1.7 |
| 11 | 18.8 | 3.7 |
| 13 | 69.0 | 0.5 |
| 14 | 14.6 | 3.8 |
| 15 | 31.8 | 1.1 |
| 18 | 28.5 | 1.1 |
| 20 | 52.0 | 0.6 |
| 21 | 25.0 | 1.2 |
| 22 | 49.6 | 1.1 |
| 24 | 51.3 | 0.4 |
| 25 | 56.1 | 0.3 |
| 28 | 68.7 | 0.6 |
| 29 | 18.8 | 2.8 |
| 32 | 17.6 | 3.4 |
| 33 | 52.2 | 0.9 |
| 36 | 0.6 | 0.5 |
| 37 | 0.7 | 0.8 |

These data shows that the compounds of the present invention have excellent brain penetration properties with low efflux ratio from the brain compartment.

Assessment of Metabolic Stability in Human Liver Microsomes (Human MST)

The metabolic stability of the compounds according to the invention may be investigated as follows:

The metabolic degradation of the test compound is assayed at 37° C. with pooled human liver microsomes. The final incubation volume of 100 μL per time point contains TRIS buffer pH 7.6 at room temperature (0.1 M), MgCl2 (5 mM), microsomal protein (1 mg/mL) and the test compound at a final concentration of 1 μM. Following a short pre-incubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LCMS/MS for the amount of parent compound. The half-life (t½) is determined by the slope of the semi-logarithmic plot of the concentration-time profile.

| Example | Human MST t1/2 [min] | Example | Human MST t1/2 > [min] |
|---|---|---|---|
| 1 | >130 | 22 | >130 |
| 2 | >130 | 24 | 31 |
| 4 | >130 | 25 | >130 |
| 5 | >130 | 26 | >130 |
| 6 | >130 | 27 | >130 |
| 8 | 73 | 28 | >130 |
| 9 | >130 | 29 | 26 |
| 10 | >130 | 30 | >130 |
| 11 | >130 | 31 | >130 |
| 12 | 25 | 32 | >130 |
| 13 | >130 | 33 | >130 |
| 14 | >130 | 35 | >130 |
| 15 | >130 | 36 | >130 |
| 16 | >130 | 37 | >130 |
| 17 | 10 | 38 | >130 |
| 18 | >130 | 39 | >130 |
| 19 | >130 | 40 | >130 |
| 21 | 37 | | |

In view of their ability to modulate the activity of $GABA_A$ receptors containing the α5 subunit and their advantageous pharmacokinetics properties the compounds of general formula (I) according to the invention, or the physiologically acceptable salts thereof, are suitable for the treatment and/or preventative treatment of all those diseases or conditions which can be influenced by modulation of $GABA_A$ receptors containing the α5 subunit. Therefore, compounds according to the invention, including the physiologically acceptable salts thereof, are particularly suitable for the prevention or treatment of diseases, particularly acute neurological disorders, chronic neurological disorders, cognitive disorders, Alzheimer's disease, memory deficits, schizophrenia, positive, negative and/or cognitive symptoms associated with schizophrenia, cognitive impairment associated with schizophrenia, bipolar disorders, autism, Down syndrome, neurofibromatosis type I, post operative cognitive decline, sleep disorders, disorders of circadian rhythms, amyotrophic lateral sclerosis, dementia caused by AIDS, psychotic disorders, substance-induced psychotic disorder, anxiety disorders, generalized anxiety disorder, panic disorder, delusional disorder, obsessive compulsive disorders, acute stress disorder, drug addictions, movement disorders, Parkinson's disease, restless leg syndrome, cognition deficiency disorders, multi-infarct dementia, mood disorders, depression, major depressive disorder, neuropsychiatric conditions, psychosis, attention-deficit hyperactivity disorder, neuropathic pain, stroke, attentional disorders, eating disorders, anorexia, anorexia nervosa, cachexia, weight loss, muscle atrophy, pain conditions, chronic pain, nociceptive pain, post-operative pain, osteoarthritis pain, rheumatoid arthritis pain, musculoskeletal pain, burn pain, ocular pain, pain due to inflammation, pain due to bone fracture, hyperalgesia, neuropathic pain, herpes-related pain, HIV-related neuropathic pain, traumatic nerve injury, recovery after traumatic brain injury, post-stroke pain, post-ischemia pain, fibromyalgia, chronic headache, migraine, tension-type headache, diabetic neuropathic pain, phantom limb pain, visceral pain and cutaneous pain.

The compounds according to the invention, including the physiologically acceptable salts thereof, are even more suitable for the treatment of i.a. cognitive disorders, post operative cognitive decline, Alzheimer's disease, schizophrenia, positive, negative and/or cognitive symptoms associated with schizophrenia, cognitive impairment associated with schizophrenia, cognitive deficits associated with Down syndrome, cognitive deficits associated with autism, cognitive deficits associated with neurofibromatosis type I, or cognitive deficits after stroke.

In a further aspect of the present invention the present invention relates to methods for the treatment or prevention of above mentioned diseases and conditions, which method comprises the administration of an effective amount of a compound of general formula (I), or the pharmaceutically acceptable salts thereof, to a human being.

The dose range of the compounds of general formula (I) applicable per day is usually from 0.1 to 1000 mg, preferably from 1 to 500 mg by oral route, in each case administered 1 to 4 times a day.

Each dosage unit may conveniently contain from 0.1 to 500 mg, preferably 1 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I, including the pharmaceutically acceptable salts thereof, will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. A list of example is: Donepezil, Memantine, Acetazolamide, Carbamazepine, Eslicarbazepine acetate, Ethosuximide, Gabapentin, Lacosamide, Lamotrigine, Levetiracetam, Brivaracetam, Nitrazepam, Oxcarbazepine, Perampanel, Piracetam, Phenobarbital, Phenytoin, Pregabalin, Primidone, Rufinamide, Sodium valproate, Stiripentol, Tiagabine, Topiramate, Vigabatrin, Zonisamide, Levodopa, Carbidopa, Haloperidol, Loxapine, Thioridazine, Molindone, Thiothixene, Fluphenazine, Mesoridazine, Trifluoperazine, Perphenazine, Chlorpromazine, Aripiprazole, Asenapine Maleate, Clozapine, Iloperidone, Lurasidone, Olanzapine, Paliperidone, Quetiapine, Risperidone, Ziprasidone and Zolpidem.

The dosage for the combination partners mentioned above is usefully ⅕ of the lowest dose normally recommended up to 1/1 of the normally recommended dose.

Therefore, in another aspect, this invention relates to the use of a compound according to the invention or a pharmaceutically acceptable salt thereof combined with at least one of the active substances described above as a combination partner, for preparing a pharmaceutical composition which is suitable for the treatment or prevention of diseases or conditions described above.

The use of the compound according to the invention in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a pharmaceutically acceptable salt thereof and at least one of the active substances described above as combination partners, optionally together with one or more inert carriers and/or diluents.

The compound according to the invention may both be present together in one formulation, for example a tablet or capsule, or separately in two identical or different formulations, for example as a so-called kit-of-parts.

The invention claimed is:
1. A compound selected from the group consisting of

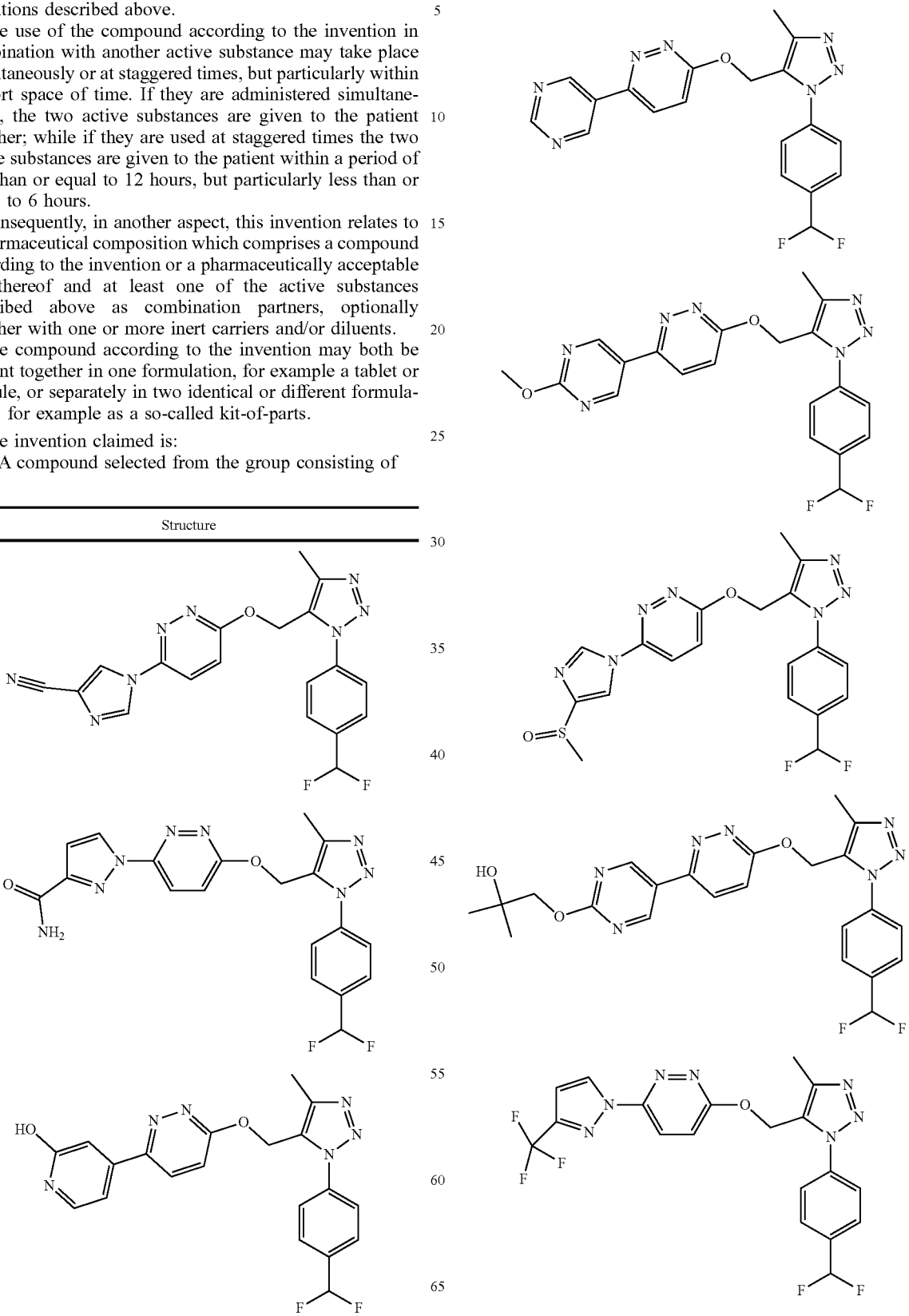

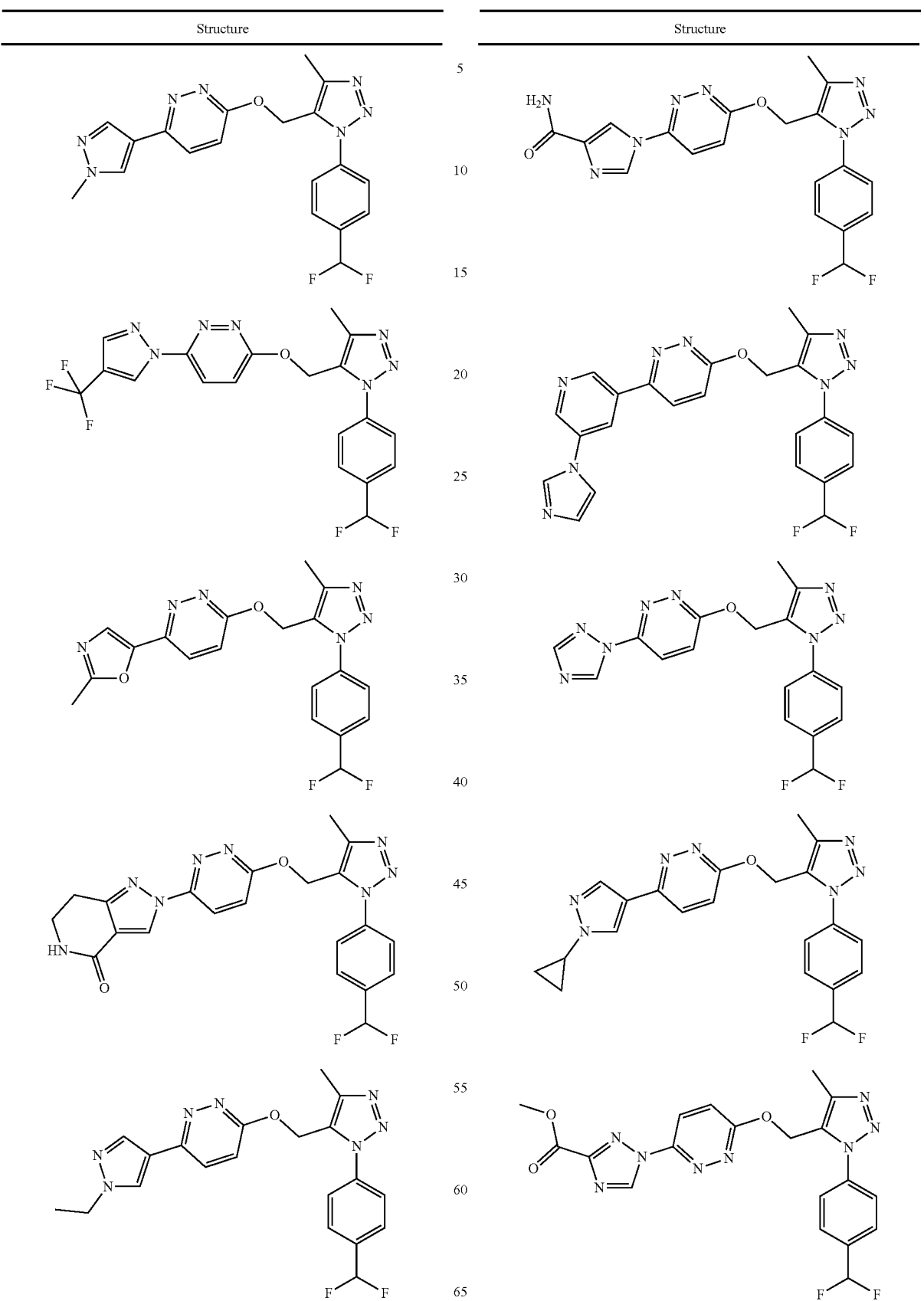

| 81 -continued | 82 -continued |
|---|---|
| Structure | Structure |
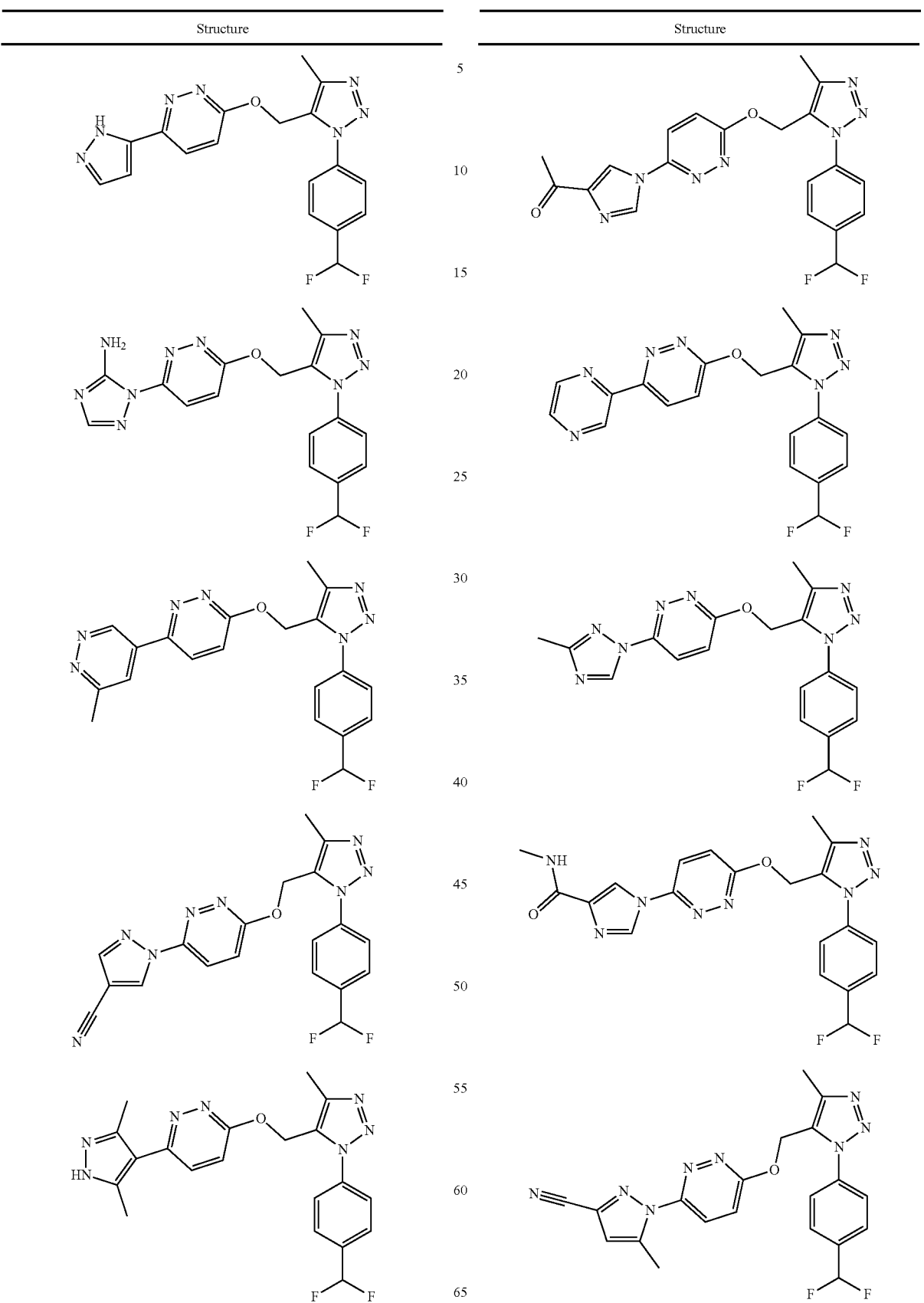

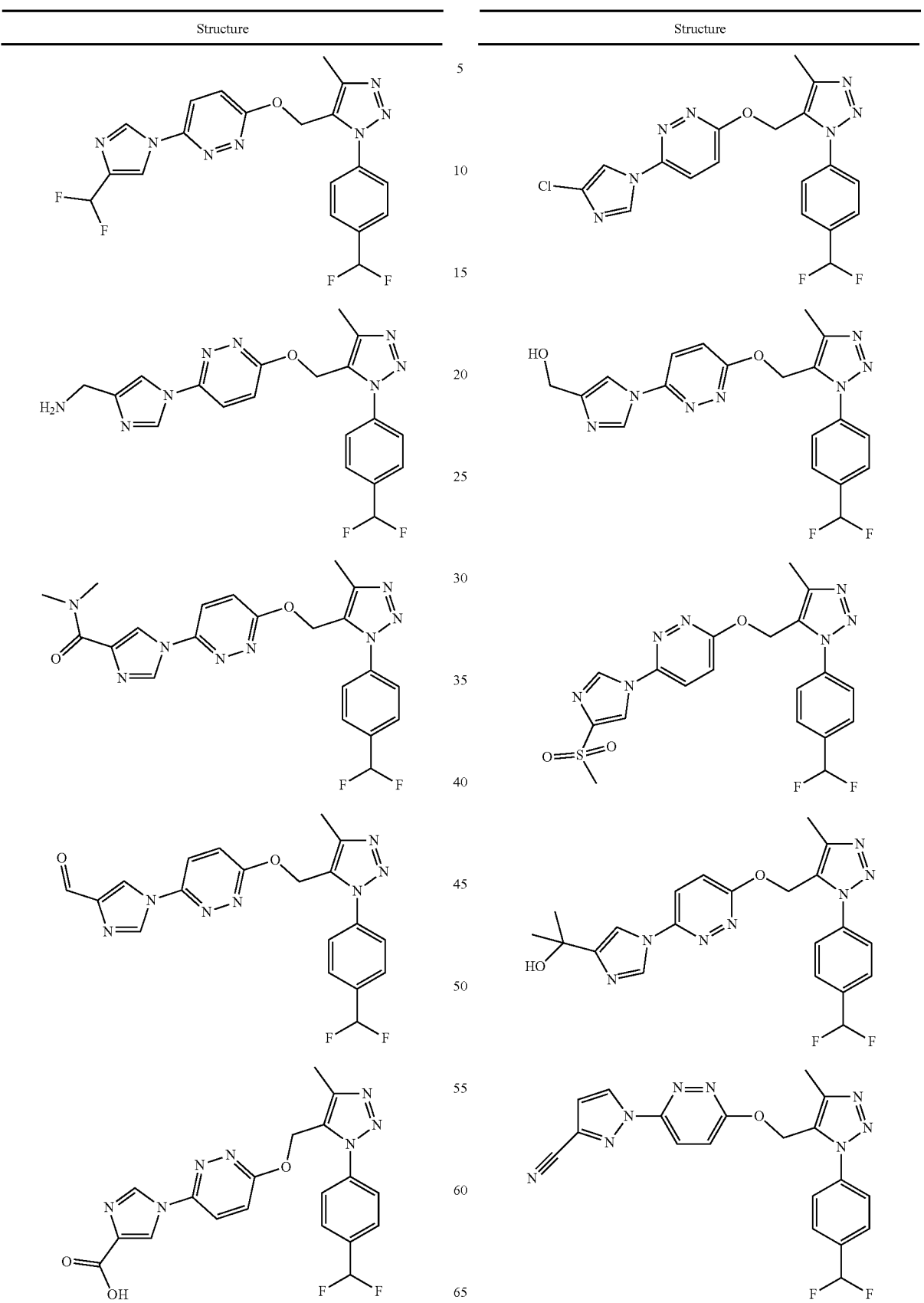

| Structure |
|---|
| 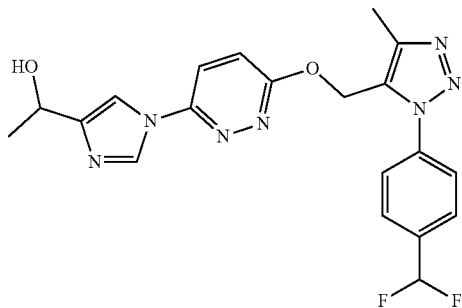 [SMILES: Cc1nnn(-c2ccc(C(F)F)cc2)c1COc1ccc(-n2cnc(C(C)O)c2)nn1] |
2. A pharmaceutically acceptable salt of the compound of claim 1.
3. A compound having the following structure
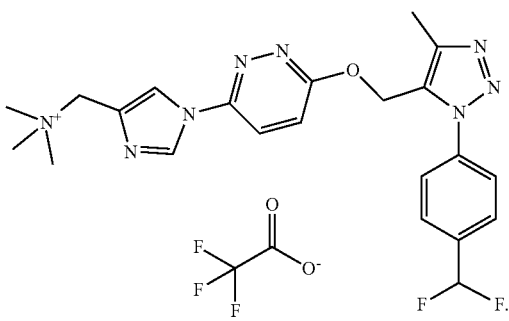 [SMILES: Cc1nnn(-c2ccc(C(F)F)cc2)c1COc1ccc(-n2cnc(C[N+](C)(C)C)c2)nn1 ; O=C([O-])C(F)(F)F]
* * * * *